(12) United States Patent
Friggens et al.

(10) Patent No.: US 7,676,346 B2
(45) Date of Patent: Mar. 9, 2010

(54) SYSTEM AND A METHOD FOR OBSERVING AND PREDICTING A PHYSIOLOGICAL STATE OF AN ANIMAL

(75) Inventors: Nic C. Friggens, Tjele (DK); Klaus Lønne Ingvartsen, Viborg (DK); Inge Riis Korsgaard, Viborg (DK); Torben Larsen, Viborg (DK); Peter Løvendahl, Ulstrup (DK); Carsten Ridder, Hornslet (DK); Nicolai Ingemann Nielsen, Viborg (DK)

(73) Assignees: Lattec I/S, Hillerod (DK); University of Aarhus, Aarhus C (DK)

( * ) Notice: Subject to any disclaimer, the term of this patent is extended or adjusted under 35 U.S.C. 154(b) by 180 days.

(21) Appl. No.: 11/870,866

(22) Filed: Oct. 11, 2007

(65) Prior Publication Data

US 2008/0255763 A1 Oct. 16, 2008

Related U.S. Application Data

(63) Continuation of application No. 10/641,167, filed on Aug. 15, 2003, now Pat. No. 7,302,349.

(60) Provisional application No. 60/403,645, filed on Aug. 16, 2002, provisional application No. 60/408,286, filed on Sep. 6, 2002.

(51) Int. Cl.
*G06F 19/00* (2006.01)
*A01J 3/00* (2006.01)

(52) U.S. Cl. ..................... 702/179; 119/14.01

(58) Field of Classification Search ............ 702/19, 702/30, 179, 22, 23, 31, 81, 83, 84, 127, 702/139, 181–183, 187; 119/14.01, 14.02, 119/14.17
See application file for complete search history.

(56) References Cited

U.S. PATENT DOCUMENTS 4,975,581 A 12/1990 Robinson et al.
5,252,829 A 10/1993 Nygaard et al.
5,442,562 A 8/1995 Hopkins et al.

(Continued)

FOREIGN PATENT DOCUMENTS

| EP | 0426232 | 9/1996 |
|---|---|---|
| EP | 0552291 | 12/1997 |
| EP | 0419223 | 5/1998 |
| EP | 1191325 | 3/2002 |

(Continued)

OTHER PUBLICATIONS

Rudi M. de Mol, Automated Detection of Oestrus and Mastitis in Dairy Cows, 2000, Thesis Wageningen University, Netherlands.*

(Continued)

*Primary Examiner*—Michael P. Nghiem
*Assistant Examiner*—Toan M Le
(74) *Attorney, Agent, or Firm*—Stephen A. Bent; Foley & Lardner LLP

(57) ABSTRACT

A system for observing and predicting a physiological state of an animal has been provided. The system includes a computer including a processor and being operatively connected to a database, at least one sample providing device for repetitively providing at least one sample of a body fluid of the animal, an analysis apparatus for analyzing the at least one sample, so as to obtain at least one sample value of at least one parameter of the body fluid, a data interface for repetitively entering the sample value of the at least one parameter in the database, where the database is adapted to store multiple database entries representing the sample value of the at least one parameter at various points in time, and where the processor is programmed to: perform at least one mathematical analysis of the at least one sample value, and selecting, on the basis of the at least one mathematical analysis, the point in time for providing a subsequent sample and performing a subsequent analysis of the subsequent sample for at least one of the parameters.

47 Claims, 14 Drawing Sheets

U.S. PATENT DOCUMENTS

| | | | |
|---|---|---|---|
| 5,729,333 | A | 3/1998 | Osten et al. |
| 5,734,587 | A | 3/1998 | Backhaus et al. |
| 5,830,133 | A | 11/1998 | Osten et al. |
| 5,983,251 | A | 11/1999 | Martens et al. |
| 6,356,857 | B1 | 3/2002 | Qin et al. |
| 6,405,672 | B1 | 6/2002 | De Mol et al. |
| 6,537,213 | B2 * | 3/2003 | Dodds ................. 600/300 |
| 6,814,025 | B2 | 11/2004 | Chen et al. |

FOREIGN PATENT DOCUMENTS

| | | |
|---|---|---|
| EP | 1191326 | 3/2002 |
| EP | 0726460 | 9/2002 |
| GB | 2354069 | 7/2004 |
| JP | 05273124 | 10/1993 |
| SE | 199902972 | 12/2000 |
| WO | 9115762 | 10/1991 |
| WO | 9605500 | 2/1996 |
| WO | 9967722 | 12/1999 |
| WO | 0039578 | 7/2000 |
| WO | 0075654 | 12/2000 |
| WO | 0114887 | 3/2001 |
| WO | WO 0114887 A1 * | 3/2001 |
| WO | 0128415 | 4/2001 |
| WO | 0140896 | 6/2001 |
| WO | 0201199 | 1/2002 |

OTHER PUBLICATIONS

F. Salehi, R. Lacroix, K.M. Wade, "Development of neuro-fuzzifiers for qualitative analyses of milk yield", Computers and Electronics in Agriculture 28 p. 171-186 (2000).

El-Saied et al. (1998): Heritability of Test Day Somatic Cell Counts and Its Relationship with Milk Yield and Protein Percentages in Dairy Ewes. J. Dairy Sci. 81: 2956-61.

K.H.M.N. Sloth, N.C. Friggens, P. Løvendahl, P.H. Andersen, J. Jensen & K.L. Ingvartsen, "Potential for Improving Description of Bovine Udder Health Status by Combined Analysis of Milk Parameters", J. Dairy Sci. 86: p. 1221-1232, American Dairy Science Association 2003.

C. Enevoldsen, J. Hindhede & T. Kristensen, "Dairy Herd Management Types Assessed from Indicators of Health, Reproduction, Replacement, and Milk Production", J. Dairy Sci. 79: p. 1221-1236 (1996).

Jonker et. al., Dairy Herd Management Practices that Impact Nitrogen Utilization Efficiency, 2002. Dairy Sci. 85, pp. 1218-1226.

Godden et al., Relationships Between Milk Urea Concentrations and Nutritional Management. Production, and Economic Variables in Ontario Dairy Herds, 2001. J. Dairy Sci. 84, pp. 1128-1139.

Godden S.M., Evaluation of a Milk Urea Assay, and the Relationship Between Milk Urea Concentrations and Nutritional Management and Performance in Ontario Dairy Herds, Nov. 1998, Doctoral Thesis, University of Guelph, ON.

P.J. Harrison et al., "Bayesian Forecasting," pp. 205-247 (1976).

A. F. M. Smith et al., "Monitoring renal transplants; an application of the multiprocess kalman filter," Biometrics 39, pp. 867-878, Dec. 1983.

Iver Thysen, "Monitoring bulk tank somatic cell counts by a multi-process kalman filter," Acta Agric. Scand. Sect. A. Animal Sci. 43; 58-64,1993.

Anders R. Kristensen et al., "Multi-level hierarchic markov processes as a framework for herd management support," Annals of Operations Research 94 (2000), pp. 69-89.

International Search Report dated Dec. 9, 2003 for Application No. PCT/DK03/00531.

* cited by examiner

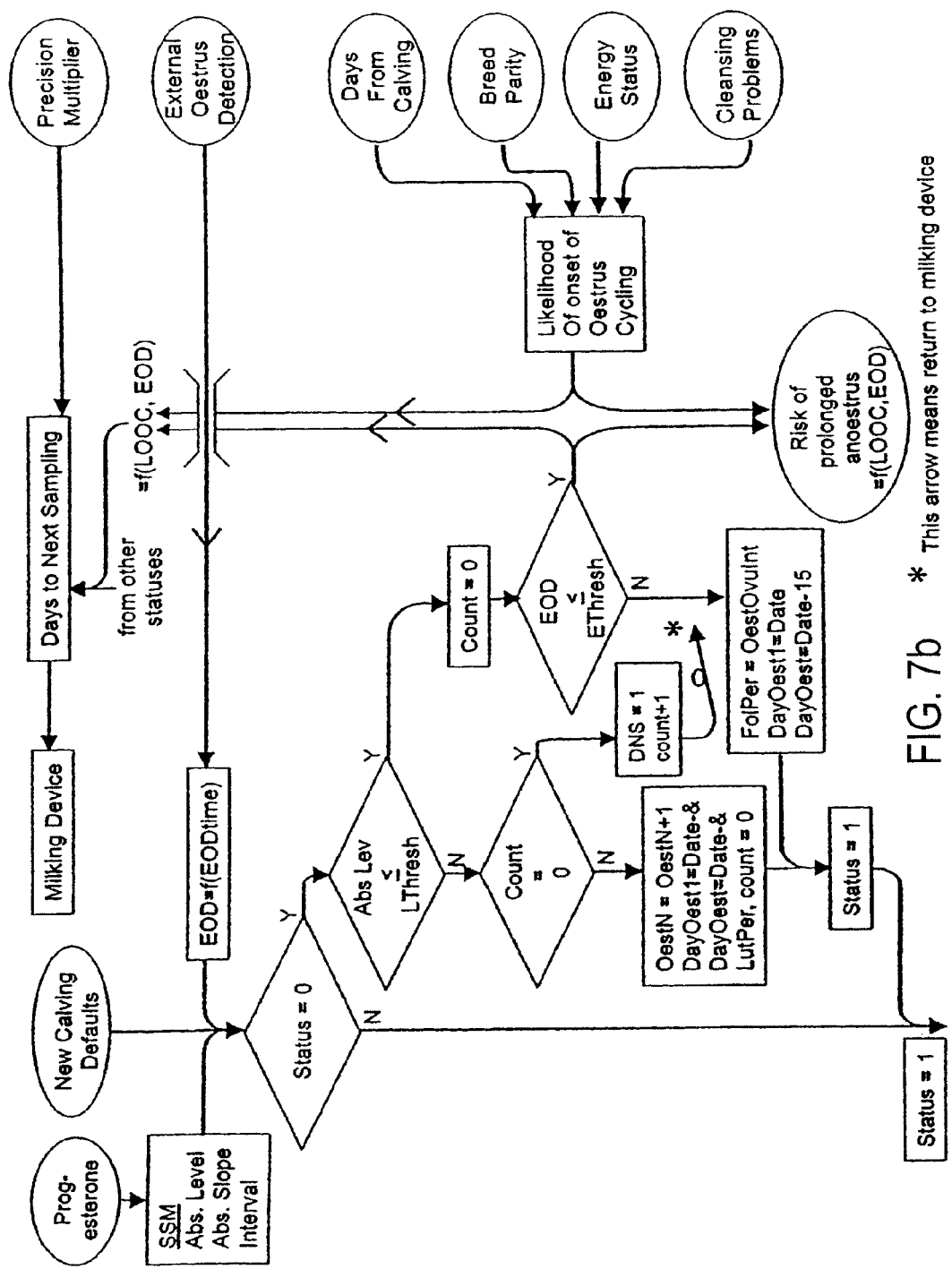
FIG. 7b  * This arrow means return to milking device

1

SYSTEM AND A METHOD FOR OBSERVING AND PREDICTING A PHYSIOLOGICAL STATE OF AN ANIMAL

CROSS-REFERENCE TO RELATED APPLICATIONS

This application is a Continuation Application of U.S. application Ser. No. 10/641,167, filed Aug. 15, 2003, now U.S. Pat. No. 7,302,349, which claims the benefit of U.S. Provisional Patent Applications 60/403,645, filed Aug. 16, 2002, and 60/408,286, filed Sep. 6, 2002, the contents of all three applications being incorporated herein by reference.

TECHNICAL FIELD

The present invention relates to systems and methods for observing and predicting a physiological state of an animal. As an example, the animal may be a cow. The systems and methods of the invention rely on a sample of a body fluid of the animal, such as urine, blood or milk.

BACKGROUND OF THE INVENTION

It is generally desirable to observe, watch and predict the physiological state of an animal, in particular a farm animal. Thus, body fluids of animals, in particular milk, urine and blood may be analysed in order to obtain values of parameters, such as cell count in milk, lactate dehydrogenase (LDH), N-Acetyl-β-D-glucosaminidase (NAGase), ketone bodies such as acetoacetate, beta-hydroxybutyrate (BHB) and acetone, urea content, progesterone, or others, each of which by itself or in combination with others indicates a certain physiological state. For example, a high LDH concentration usually indicates mastitis, whereas the progesterone content may indicate a pregnancy state.

The prior art has proposed various methods for analysis of milk samples. For example, U.S. Pat. No. 5,252,829 discloses a method for determining the amount of urea in milk. In a milk sample, the absorption of infrared radiation in various wavelength intervals are determined, whereby urea, fat, lactose, and protein absorb in different wavelength intervals.

U.S. Pat. No. 6,405,672 and de Mol (2000) discloses a system and a method for monitoring the physical condition of a herd of livestock, errors between values predicted in accordance with a time-series model and corresponding measured values are used for determining a confidence interval for a prediction for each animal individually the significance of an error between a prediction and a measured value regarding the likelihood that the animal is in heat or suffers from a disease is automatically assessed for each animal individually.

SUMMARY OF THE INVENTION

With the aim of providing an improved tool for observing and predicting a physiological state of an animal, a first aspect of the present invention provides a system for observing and predicting a physiological state of an animal, the system comprising:
 a computer comprising a processor and being operatively connected to a database,
 at least one sample providing device for repetitively providing at least one sample of a body fluid of the animal,
 an analysis apparatus for analysing the at least one sample, so as to obtain at least one sample value of at least one parameter of the body fluid,
 a data interface for repetitively entering the sample value of the at least one parameter in the database, wherein the database is adapted to store multiple database entries representing the sample value of the at least one parameter at various points in time, and wherein the processor is programmed to:
 perform at least one mathematical analysis of the at least one sample value, and
 selecting, on the basis of the at least one mathematical analysis, the point in time for providing a subsequent sample and performing a subsequent analysis of said subsequent sample for at least one of the parameters.

In a second aspect, the present invention provides a method for observing and predicting a physiological state of an animal, the method comprising:
 repetitively providing at least one sample of a body fluid of the animal,
 analysing the at least one sample, so as to obtain at least one sample value of at least one parameter of the body fluid,
 entering the sample value of the at least one of parameter in a database of a computer system, whereby the database is loaded with multiple database entries representing the sample value of the at least one parameter at various points in time, and
 performing at least one mathematical analysis of the at least one sample value, and
 selecting, on the basis of the at least one mathematical analysis, the point in time for providing a subsequent sample and performing a subsequent analysis of said subsequent sample for at least one of the parameters.

In the mentioned systems and methods the mathematical analysis is preferably a statistical method.

The statistical analysis is preferably selected from the group consisting of a univariate analysis of the database entries to obtain a first set of data representing expected sample values of at least one of the parameters at future points in time or a multivariate analysis of the database entries to produce a second set of data derived from combined analysis of sample values of at least two parameters. The first and second sets of data can be combined to obtain a third set of data representative of the physiological state of the animal and the obtained first, second and third sets of data may be stored in the database.

The types of univariate analysis and multivariate analysis useable in the present invention are disclosed by the non-limiting examples mentioned later in the specification.

In order to improve the measurement of at least one parameter for observing and predicting a physiological state of an animal the database comprises at least one external value of at least one external parameter. The external parameter is disclosed later in the specification.

In an embodiment of the present invention at least one external parameter is included in the database, such as at least 2 external parameters, e.g. at least 3 external parameters, such as at least 4 external parameters, e.g. at least 5 external parameters, such as at least 6 external parameters, e.g. at least 10 external parameters, such as at least 15 external parameters, e.g. at least 25 external parameters, such as at least 50 external parameters.

The system is programmed to and the method further comprises the step of performing data analysis of the database entries to obtain an indication of the physiological state of the animal, whereby the external value is included in the data analysis.

It is highly advantageous that an ideal production performance monitoring system and a method is capable of generating quantitative analytical data for selected parameters for which even relatively small day-to-day variations are highly predictive for a change in e.g. the overall health condition, the physiological condition, nutritional and energy state, the state in the oestrus cycle or pregnancy of the individual population member being tested. This requires that the system provided permits frequent quantitative analyses to be made at a cost-effective level.

Furthermore, it is an advantageous feature of the invention that the parameters can be analysed in a dynamic and intelligent mode, i.e. that only those parameters which, at a given point in time of the reproduction and/or lactation cycle of the individual population members should be analysed in a particular milk sample. This is achieved by providing a computer system for storing data including data for the physiological and nutritional state of said each population individual member including data indicating point in time in the reproduction and lactation cycles. An analysis apparatus for analysing a plurality of parameters in a sample is generating a detectable signal in the presence of an individual sample parameter. The determination of whether a parameter shall be analysed or not is being controlled by the computer having data stored for the physiological and nutritional state of each individual population member such that the analysis is only activated at selected points in time or at selected time intervals. In this connection, one interesting feature is that the computer having data stored for the physiological and nutritional state of each individual population member is continuously updated with new data, so that the selection of the range of parameters that are analysed in a given sample at a given point in time is based on a constantly updated set of data for the particular population member.

The system and the method may select, on the basis of the at least one mathematical analysis, the point in time for providing a subsequent sample and performing analysis of said subsequent sample for at least one of the parameters. This selection is e.g. provided by as soon as the sample value of a selected parameter differ by more than a given deviation measure X, from the expected sample value the sample frequency will be increased for measuring the selected parameter. In the situation where the sample value of the selected parameter is not differing by more than the given measure X from the expected sample value, the sample frequency may be decreased for measuring the selected parameter. The deviation measure X may be a relative measure or an absolute measure. The aforementioned deviation measure may easily be determined in accordance with mathematical and statistical methods well known to a person skilled in the art.

In another aspect, the invention provides a system for observing and predicting a physiological state of an animal, the system comprising:

a computer comprising a processor and being operatively connected to a database, at least one sample providing device for repetitively providing at least one sample of a body fluid of the animal, an analysis apparatus for analysing the at least one sample, so as to obtain at least one sample value of each of a plurality of parameters of the body fluid, a data interface for repetitively entering the sample value of each of the parameters in the database, wherein the database is adapted to store multiple database entries representing the sample value of each of the parameters at various points in time, and wherein the processor is programmed to:

perform a univariate analysis of the database entries to obtain a first set of data representing expected sample values of at least one of the parameters at future points in time, perform a multivariate analysis of the database entries to produce a second set of data derived from combined analysis of sample values of at least two of the parameters, combine the first and second sets of data to obtain a third set of data representative of the physiological state of the animal, and store the first, second and third sets of data in the database.

The benefits of univariate and multivariate data analysis are utilised in order to more precisely predict or observe the physiological state by taking into account a plurality of parameters. Thus, an accurate analysis is made, which results in an indication of a current state, with a view to make it possible to predict future states. Embodiments of the system of the invention may be arranged close to the animals, for example in a milking parlour of a farm, and they may be operable by a farmer or a farm technician. Accordingly, initial indications of the physiological state of, e.g. cows in a herd, may be provided to a farmer without the farmer having to involve a veterinarian in the initial assessment of the physiological state of, e.g. a cow.

In the present context, the term "physiological state" should be understood as a state in a general sense. For example, it may be a state with respect to health, including state with respect to clinical or subclinical diseases, reproduction, or energy status.

In the present context, the term "population" refers to a relevant group of animals, e.g. a particular herd, a particular breed, a group of herds with similar characteristics such as production system, a regional or a national population.

The term "univariate data analysis" refers to data analysis in which data relating to a single variable are analysed. The univariate data analysis may comprise analysis of correlated univariate variables.

The term "multivariate data analysis" refers to data analysis in which data relating to at least two variables are analysed.

It should be understood that a result from the univariate or multivariate analysis may be used as an input for further analysis. The further analysis may be univariate or multivariate. For example, the output from a Principal Component Analysis (PCA) may be used as an input for a State Space Model (SSM) or vice versa.

In a further aspect, the invention provides a method for observing and predicting a physiological state of an animal, the method comprising:

repetitively providing at least one sample of a body fluid of the animal, analysing the at least one sample, so as to obtain at least one sample value of each of a plurality of parameters of the body fluid, entering the sample value of each of the parameters in a database of a computer system, whereby the database is loaded with multiple database entries representing the sample value of each of the parameters at various points in time, and performing a univariate analysis of the database entries to obtain a first set of data representing expected values of at least one of the parameters at future points in time, performing a multivariate analysis of the database entries to produce a second set of data derived from combined analysis of sample values of at least two of the parameters, and combining the first and second sets of data to obtain a third set of data representative of the physiological state of the animal, and storing each of the first, second and third sets of data in the database.

The computer and the database need not be located in the same physical location. For example, the computer, including the processor, may be comprised in an analysis apparatus provided near an animal herd, for example in a stable, whereas the database may be comprised in a personal computer in an office separate from the stable, or in a mainframe located at a remote data processing facility.

In yet a further aspect, the invention provides a method for observing and predicting a physiological state of an animal, the method comprising:

entering at least one external value of at least one external parameter in a database of a computer system, repetitively providing at least one sample of a body fluid of the animal, analysing the at least one sample, so as to obtain at least one sample value of each of a plurality of parameters of the body fluid, entering the sample value of each of the parameters in the database, whereby the database is loaded with multiple database entries representing the sample value of each of the parameters at various points in time, and performing data analysis of the database entries to obtain an indication of the physiological state of the animal, whereby the external value is included in the data analysis.

A system for performing the method is also provided.

The at least one external parameter may comprise at least one of: the age of the animal, the breed of the animal, the weight of the animal, the reproduction history of the animal, feeding particulars, season, geographical location, identification to the herd of origin, sample yield, duration of sample flow, sample temperature, electrical conductivity of the sample, cell count of the sample, residues of antibiotics in the sample, fat content of the sample, protein content of the sample, bacteriological examination of the sample, activity of the animal, animal behaviour, feed intake, body temperature, blood composition, vaginal mucus resistance of the animal, breath and noise.

In the present context, the term "identification to the herd of origin" relates to the recognition of a single animal or a herd of animals in order to use the information in other systems either at the same location or at distant locations.

By taking into account external data, more accurate predictions may be made, and the number of models to be employed in multivariate data analysis may be reduced.

In another aspect the invention relates to a method and a system for observing and predicting a physiological state of an animal, the method comprising:

repetitively providing at least one sample of a body fluid of the animal, analysing the at least one sample, so as to obtain at least one sample value of each of a plurality of parameters of the body fluid, entering the sample value of each of the parameters in a database of a computer system, whereby the database is loaded with multiple database entries representing the sample value of each of the parameters at various points in time, and performing State Space Model (SSM) analysis of the database entries to obtain data representative of the physiological state of the animal.

The invention also provides a method and a system for observing and predicting a physiological state of an animal, the method comprising:

repetitively providing at least one sample of a body fluid of the animal, analysing the at least one sample, so as to obtain at least one sample value of each of a plurality of parameters of the body fluid, entering the sample value of each of the parameters in a database of a computer system, whereby the database is loaded with multiple database entries representing the sample value of each of the parameters at various points in time, and performing a multivariate projection analysis of the database entries to obtain data representative of the physiological state of the animal.

Specific embodiments and features of the aspects of the invention are apparent from the appended claims and the below detailed description of the invention. It should be understood that the below description is in no way limited to particular aspects of the invention. Rather, the discussion applies equally well to any aspect of the invention.

BRIEF DESCRIPTION OF THE DRAWINGS

The invention will now be further described with reference to the drawings, in which:

FIGS. 7a-7d shows information flow according to an embodiment of the present invention when analysing for progesterone and reproduction.

DETAILED DESCRIPTION OF THE DRAWINGS

Figure 1:
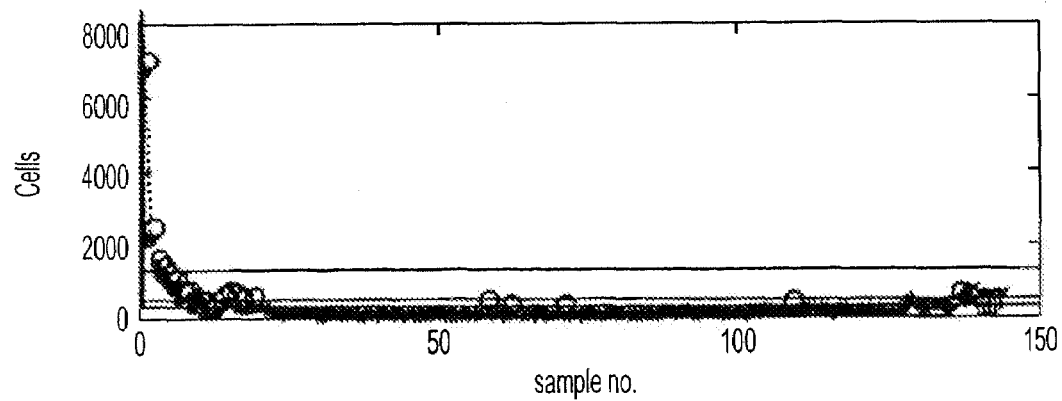
FIGS. 1 and 2 illustrate measured cell counts vs. analysis data for various cows, FIG. 3 contains a chart (chart A) of simulated data and charts (charts B, C and D) representing output from an extended multiprocess Kalman filter.

One tool for multivariate data analysis is Principal Component Analysis (PCA), in literature also referred to as "factor analysis". In short, manifest variables are substituted by latent variables in multivariate data analysis. Manifest variables are direct and measurable, i.e. manifested variables, in the present context also referred to as sample values, such as fat- or lactose concentration in milk. Latent variables are weighted sums of the manifest variables. As an example, latent variables $t_1$ and $t_2$ are determined as $t_1=0.45*$fat %+0.12*lactose %, and $t_2=0.05*$fat %+0.72*lactose %. Here, $t_1$ and $t_2$ are projections of the manifest variables, fat % and lactose %, on a vectors [0.45; 0.12] and [0.05; 0.72]. By appropriate selection of weightings, e.g as eigenvectors of a matrix of manifest variables, the thus determined latent variables include information from all of the manifest variables independently from the number of manifest variables. Accordingly, information in an aggregation of data may be distinguished or separated from random noise. Moreover, the weightings may be visualised, so as to enable extraction of information related to the manifest variables, and the latent variables may be visualised, so as to enable extraction of information concerning objects, for example animals, such as cows, on which measurements have been performed.

The manifest variables may be provided by using any analytical means known in the art. Illustrative examples of such analysing means includes enzyme based assays, immunologically based assays, biosensors, biochemical assays, spectrometric assays, wet chemistry assays, sequential injection analysis and flow injection analysis assays which are suitable for the analysis. Preferably, the analysing means are designed to perform quantitative measurements. In one useful embodiment the analysing means comprises solid support analytical means or devices which e.g. may be in the form of test strips (also known as dry sticks) comprising appropriate reagent(s) that in the presence of the compound being analysed generate(s) a detectable signal. Additionally, the analysing means may comprise or may be operationally linked to means for storing and transporting such solid support analytical devices.

The aggregation of data may conveniently be arranged or stored in a table in the database. For example, measured variables may be arranged in columns of the table, and the objects, e.g. identifications of cows, may be arranged in rows. This table is referred to as X. In PCA, the above-mentioned weightings can be the elements in the eigenvectors to the correlation matrix of X. The number of relevant eigenvectors, which governs the number of relevant latent variables, is dependent from the content of information in X. As an example, table sizes of 30–1000×20 could yield a number of latent variables of, e.g. 2 to 30, such as 2 to 20, usually 2 to 8.

A physiological state of an animal, such as the animal's health state, may be determined from a comparison of a pattern in measured parameters, i.e. sample values, and a reference pattern (or a reference parameter value) which is typical for healthy animals and a pattern which is typical for animals suffering from a certain disease, respectively. Once an aggregation of data covering all physiological states to be observed or predicted is available, probabilities of a particular animal belonging to the various states may be determined. If for example, sample values of a particular cow are determined during and after milking of the cow, the cow may be classified, and appropriate measures may be taken.

In multivariate data analysis, so-called patterns of parameters (i.e. manifest variables) may be provided in order to take into account mutual influences between parameters. If a selective parameter is at hand, univariate data analysis may be appropriate. As an example, one progesterone measurement may in most cases give a satisfactory indication of oestrus or heat, and pregnancy. However, it has been found that very few parameters are purely selective for the physiological state of, e.g. a cow, and a qualified assessment is in most cases only possible following an analysis of sample values of several parameters. For example, a high level of urea in milk may indicate one state if the fat concentration is high, and another state if the fat concentration is low, while an increasing or decreasing milk yield may indicate yet third and fourth states.

In order to predict the contents of somatic cells in milk, a mathematical method, such as PLSR (Partial Least Squares Regression), may be employed, for analysing an Infrared (IR) spectrum of milk. It has been found that such a model is suitable for establishing a basis of experience for each individual animal in a herd.

In order to establish a basis of experience which is global, i.e. not specific for an individual animal but generally applicable to all animal of a certain kind, e.g. cows, chemometric classification methods may be applied. One such method is the so-called Soft Independent Modeling of Class Analogies (SIMCA), in which previous (or historical) sample values are grouped in classes, whereby the classes are analysed individually by means of PCA. Thus, historical sample values may for example be grouped in one class representing healthy cows, and another class representing sick cows. A model for each class may exist, and by applying new sample values to the models of the various classes, it may determined to which class the cow in question belongs. However, such a methodology does not take into account external data, such as race, age, feeding particulars, season, geographical location, etc. which may influence the sample data.

Therefore, an "inverse SIMCA" has been developed in which one separate model is established for each healthy animal. If a new measurement does not resemble any one of the patterns of healthy animals, the probability of the animal in question being sick is high. Thus, by introducing a plurality of separate models, wider limits are created for what is regarded as a normal state which also reflects the biological reality.

However, the number of models may be reduced, or reliability of analysis results increased, by including the external data in the models.

In one embodiment of the models, the animals are grouped by their calving time. A healthy state, i.e. no mastitis, is defined by a cell count of less than 200. The analysis only includes animals for which the number of observations with a low cell count is at least 30. This results in a total of 121 models which are based on 19 variables or parameters: milk yield, FPD and Conductivity, as well as relative and absolute values of Fat A, Fat B, Protein, Lactose, Urea, Citric acid, Lactate Dehydrogenase (LDH), Total solids (TS) and Solids Non Fat (SNF). The measured cell count is not included in the models. As the variance span for the measured parameter values varies, an auto scaling of the sample values is performed before the eigenvectors are computed.

Mathematically, the models may be expressed as:

$$X = T_a * P_a' + E$$

wherein X represents the scaled data, T represents the latent variables (the projection of X on P), P is the eigenvector of the correlation matrix X'X, and E is a residual matrix which collects random noise. The subscript a indicates the dimension of the model. The dimension is found by cross validation and is also referred to as the complexity, the number of latent variables, number of factors or the range of X'X. In the present context, a is typically at least 2 and at the most 8.

For each cow and for each milking (indexed by i), the 19 variables are sampled in a pattern $x_i$, and the projection of $x_i$ on each of the models is determined:

$$t_i = x_i * P$$

In order to ensure an independent validation, i.e to ensure globality, models based on the animal in question itself are omitted.

Leverage, denoted h (corresponding to Hotelling's $T^2$), and residual, r, are subsequently determined. Geometrically, the leverage represents the distance from the 19-dimensional point of measurement to the point of projection in the model. The leverage is computed as the square sum of the elements in $t_i$, and the residual is computed as the square sum of the elements in the vector $x_i - t_i * P'$. The quantities h and r are normalised with their respective 95% significance levels from the modelling phase. The final test quantity is the length of the vector (h,r), and $x_i$ is regarded as belonging to the model if this quantity is less than $\sqrt{2}$.

Figure 2:
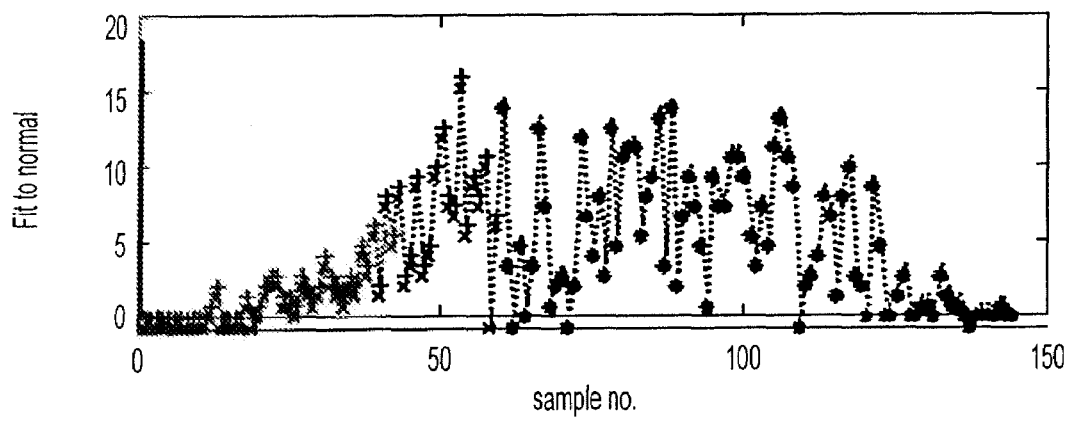
Figure 3A:
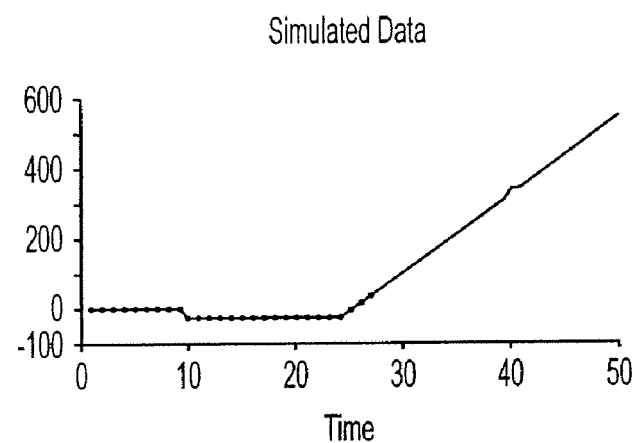
Figure 3B:
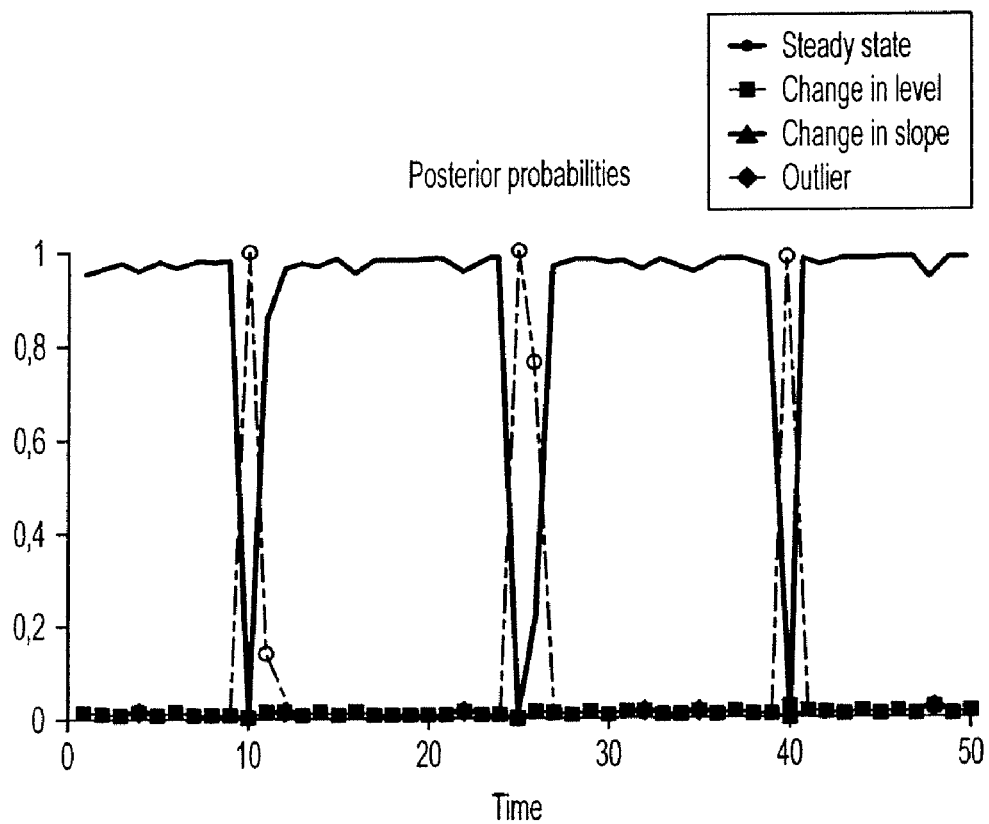
Figure 3C:
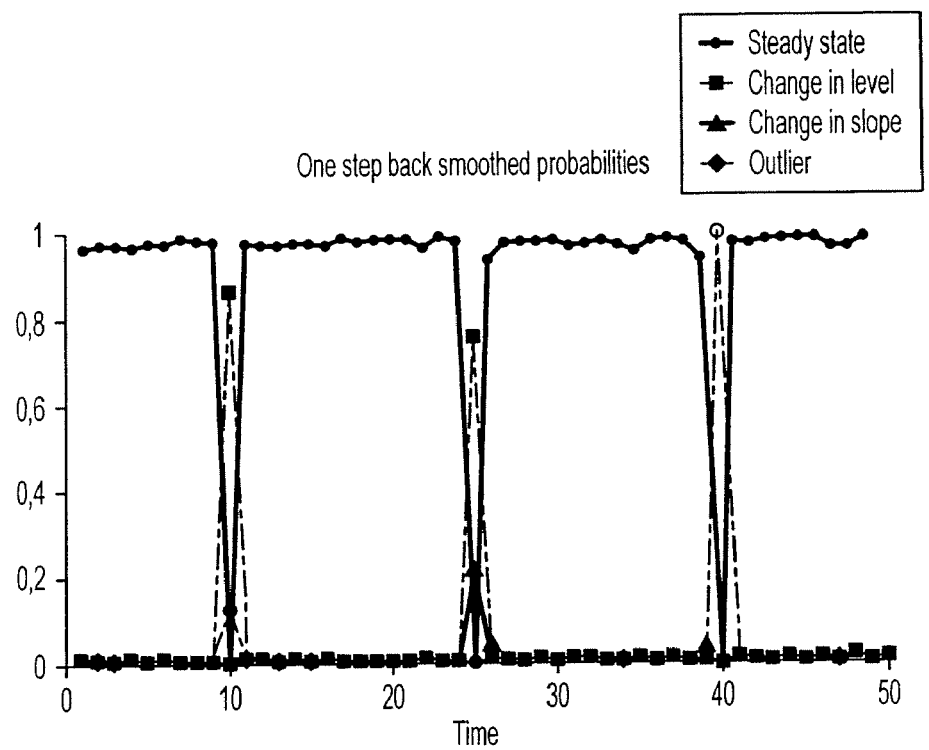
Figure 3D:
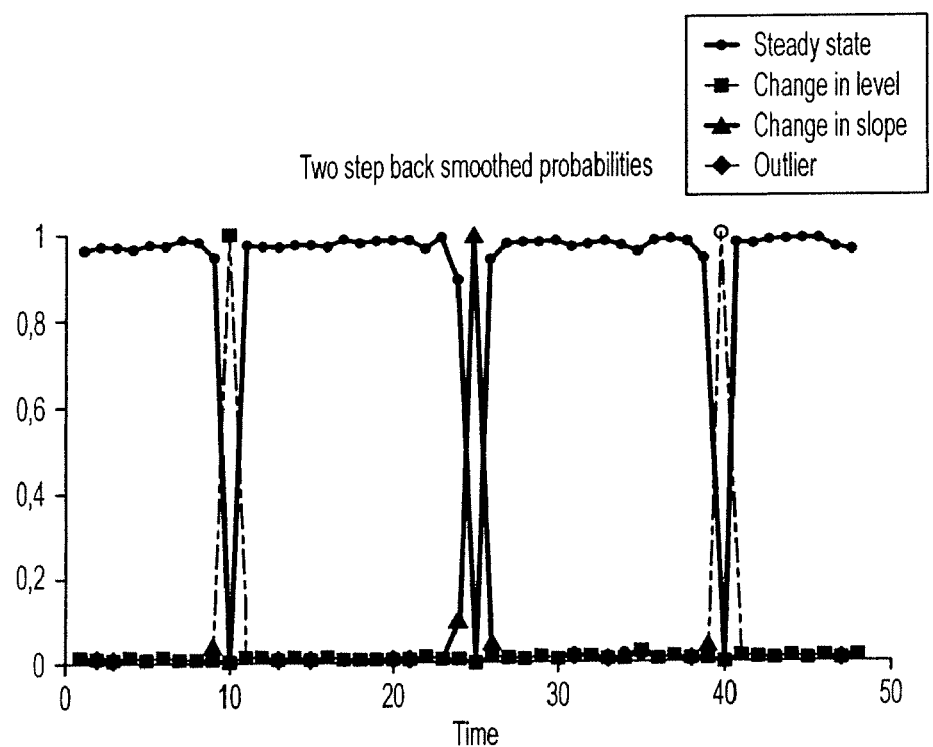

FIGS. 1 and 2 illustrate measured cell counts vs. analysis data for various cows. The "fit to normal" data are obtained as 100*[(the number of models to which a certain milking belongs)/(the total number of models)]. Thus, if a milking belongs to 14 out of 118 models, the "fit to normal" value is 100*14/118=11.9. The cell count in FIG. 1 represents measured cell counts. As illustrated in FIGS. 1 and 2, when the cell count is high, the models based on low cell counts do not fit well, whereas when the cell count is low, the models fit well. It has been found that the inclusion of fat, protein, solids and SNF (Solids Non-Fat) in the models appear to improve the discrimination ability of the models.

As it will be understood from the above disclosure, one example of the physiological state of a cow is whether or not the cow suffers from mastitis. In an SSM for predicting and diagnosing mastitis, the input to the models may include somatic cell count data.

SSMs have been developed for following a process developing over time. This process may either follow a pre-planned route or deviate from that. The deviations could represent either a usually high measurement error, also referred to as an outlier, or a change in the systematic part of the process.

As indicated above, somatic cell count is an accepted indicator of mastitis. However, measurements of cell count are subject to noise and outliers, which decrease their potential use in decision support. Statistical tools to separate noise from biologically relevant changes can help improving the interpretation of somatic cell count (SCC) data. The extension (Smith and West, 1983) of the multiprocess Kalman filter (Harrison and Stevens, 1976) to provide probabilities of different kinds of changes may be used in decision support—for example an action of treatment should be taken if the probability of an increase in SCC is above a critical level. Thus, there is provided a dynamic linear model and the multiprocess class II mixture model with recursive updating procedure for providing probabilities of different kinds of changes.

Model

Dynamic linear model. For the time series $\{y_t\}_{t=1,\ldots,n}$ consisting of n observations (of e.g. ln(somatic cell count)) a dynamic linear model (DLM) is described by an observation equation:

$$Y_t = F_t \theta_t + v_t$$

a system equation:

$$\theta_t = G_t \theta_{t-1} + w_t$$

and initial information:

$$\theta_0 \sim N(m_0, C_0)$$

where $F_t$ is the observation matrix, $\theta_t$ is a latent vector (or scalar) and $v_t$, with $v_t \sim N(0, V_t)$, is the observation noise. The latent process $\{\theta_t\}_{t=1,\ldots,n}$ is given by the system equation (and the initial information) with evolution matrix (system matrix) $G_t$ and evolution error $w_t$. It is assumed that $w_t \sim N(0, W_t)$, with $v_1, \ldots, v_n, w_1, \ldots, w_n$ mutually independent and independent of the initial information. The model specified by $\{F_t, G_t, V_t, W_t\}$ will be denoted $M_t$.

Example: The sire model given by $Y_t = s + e_t$, for $t=1, \ldots, n$; with $s \sim N(0, \sigma_s^2)$ independent of $e = (e_1, \ldots, e_n)' \sim N_n(0, 1_n \sigma_e^2)$ is equivalent to the DLM given by observation equation $Y_t = s_t + e_t$, system equation $s_t = s_{t-1}$ and initial information $s = s_0 \sim N(0, \sigma_s^2)$. Note that $F_t = G_t = 1$ and $V_t = \sigma_e^2$, for $t=1, \ldots, n$; $m_0 = 0$ and $C_0 = \sigma_s^2$, and the model is without evolution error.

Multiprocess class II mixture model: If the observations do not follow the same DLM for all values of t, it is useful to introduce mixture models, where, at each time t, we may choose between J different models. The Multiprocess class II mixture model is defined as follows: Let, for some integer J>1, $A = \{\alpha_1, \ldots, \alpha_J\}$ denote the parameter space for $\alpha$, and suppose, that at each time t, there exist an $\alpha \in A$ so that $M_t(\alpha)$ holds. If the value, $\alpha_j$, of $\alpha$ defining the model at time t, $M_t(\alpha_j)$, is selected with known probability, $\pi_t(j) = P(M_t(\alpha_j)|D_{t-1})$, then the series $\{Y_t\}_{t=1,\ldots,n}$ is said to follow a multiprocess class II mixture model. We will use $M_t(j)$ as short notation for $M_t(\alpha_j)$. Furthermore we let $D_t$ denote the information available at time t, $t \geq 0$. Here we will assume that $D_t = D_{t-1} \cup \{Y_t\}$ for $t>0$.

Multiprocess Kalman filter (extended): In the following we outline the recursive updating procedure for providing posterior probabilities $P(M_t(j)|D_t)$, of model j at time t, as well as one and two step back smoothed probabilities, $P(M_{t-1}(j)|D_t)$ and $P(M_{t-2}(j)|D_t)$, for the different models at different time points. The procedure is outlined for a model with J=4, $G_t = G$ and $F_t = F$ for all t. The observation error as well as system error are assumed to depend on the model at time t, but are otherwise independent of time. Model j is assumed to be selected with probability $P(M_t(\alpha_j)|D_{t-1}) = \pi_0(j)$ independently of the past, $D_{t-1}$, $j=1, \ldots, 4$ (fixed model selection probabilities). A priori it is assumed that $\theta_0 \sim N(m_0, C_0)$ and that all of the parameters are known. For t=1: From the system equation and the prior distribution of $\theta_0$ we obtain $\theta_1|M_1(j), D_0 \sim N(Gm_0, GC_0G' + W(j))$ for $j=1, \ldots, 4$. This, together with the observation equation, gives, conditional on $M_1(j)$, the forecast distribution of $Y_1$:

$$Y_1|M_1(j) \sim N(FGm_0, F(GC_0G' + w(i))F' + v(j))$$

Next, the posterior probability of the different models at time 1 are calculated from $$P(M_1(j)|D_1) \propto p(y_1|M_1(j))P(M_1(j)|D_0)$$

where $P(M_1(j)|D_0)$ by assumption is equal to $\pi_0(j)$. The posterior distribution of $\theta_1$ is then given by a mixture of $\theta_1|M_1(j), D_1 \sim N(m_1(j), C_1(j))$, $j=1, \ldots, 4$ with mixture probabilities $P(M_1(j)|D_1)$; For time t>1. The steps in obtaining the (an approximate) posterior distribution of $\theta_t$, as well as one (and two) step back smoothed probabilities of the different states/models at time t−1 (t−2 for t>2) become more involved. Here we refer to Smith and West (1983) for further details.

In the following non-limiting embodiments of the present invention cows are used as non-limiting illustrating examples of the type of animal useable in the present invention and milk used as non-limiting illustrating examples of the type of body fluid useable in the present invention.

These embodiments also illustrates that the selection into the groups Indicator based risk and Additional risk factor, of the different factors involved may be a dynamic process and that it is obvious for the person skilled in the art how to provide minor or larger modifications and changes.

EMBODIMENTS OF THE PRESENT INVENTION

General Application of the Present Invention

Figure 4:
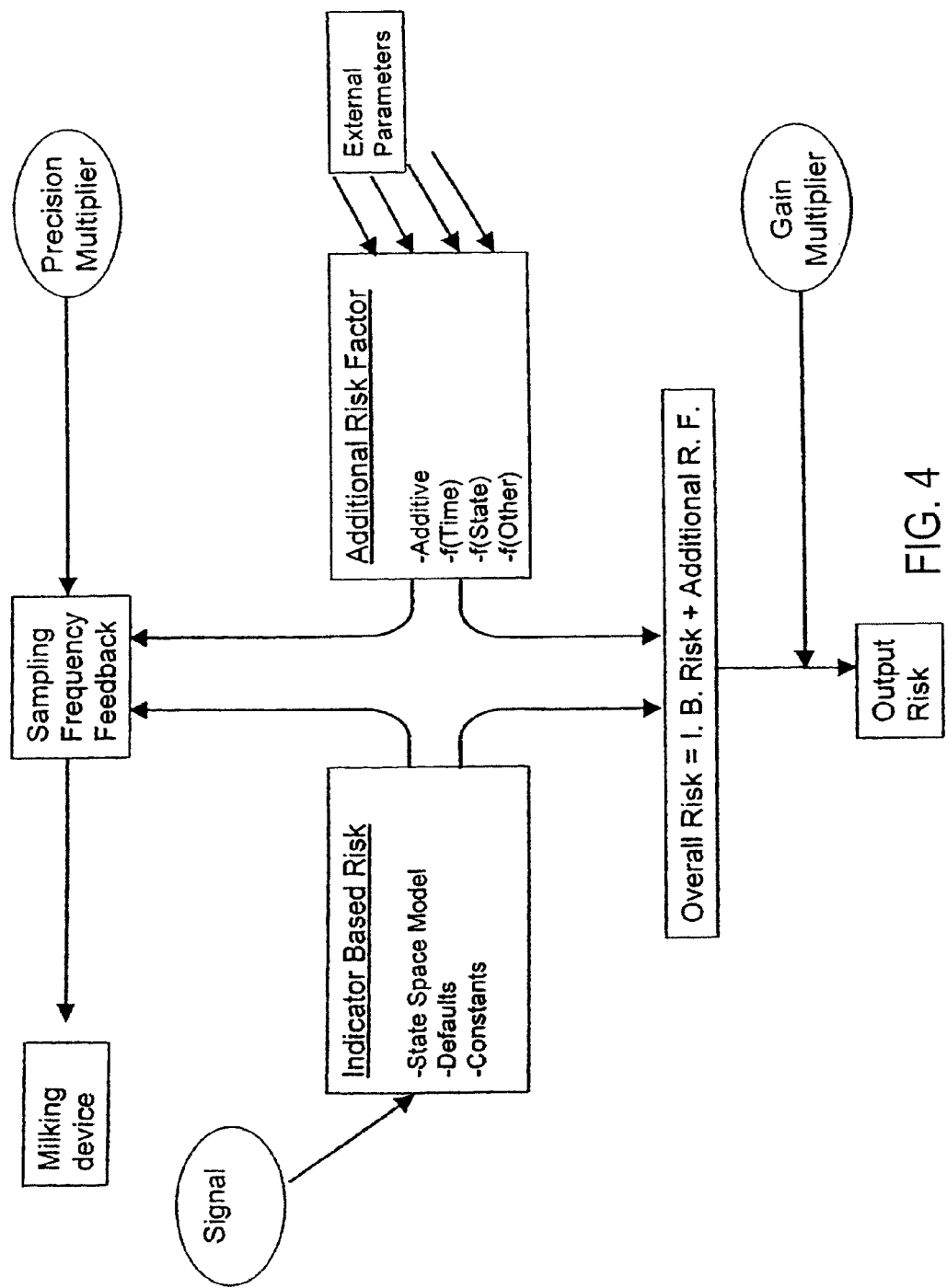
FIG. 4 shows a general diagram of the information flow according to the present invention.

In a preferred embodiment of the present invention the general design, as shown in FIG. 4, has, in as far as this is possible, been applied to each particular model. The models have 2 major outputs; an overall risk (or likelihood of an event) presented to the user, and a calculation of when to take the next sample that feeds back to the analysis apparatus. 2 Modules generate these outputs; one using only the information provided by the signal coming from the analysing apparatus, the other combining diverse additional information into an additional risk factor. This structural separation is designed to make it easier to test the different components of the model and incorporate further developments. It also reflects the underlying logic that additional risk factors are only those factors whose effects are not acting on the signal being measured. In other words, if the effect of body fat mobilisation is fully reflected in BHB levels then body fat mobilisation should not be included as an additional risk factor.

Two additional features are incorporated to allow the model to be adjusted to local conditions, a precision multiplier and a gain multiplier. The precision multiplier allows the accuracy of the risk assessments to be modulated according to local requirements. An example of this could be a dairy farmer who supplies milk for cheese making and thus has more stringent requirement to reduce mastitis in his herd. The precision multiplier will allow him to increase his sampling frequency and thus the precision of the risk as measured by the analysing signal.

The gain multiplier will allow the sensitivity of the model to be adjusted. An example of this could be a farm or region where the feeding was such that BHB levels were systematically higher than the universal norm and consequently an unacceptably large number of animals were being identified as at risk of ketosis. The gain multiplier could be then used to decrease the sensitivity of the risk assessment to fit with prior experience of ketosis incidence in this herd. Whether or not this facility will be widely used, or whether it should be accessible by the user, remains to be determined but it is included in the model architecture.

Figure 5A:
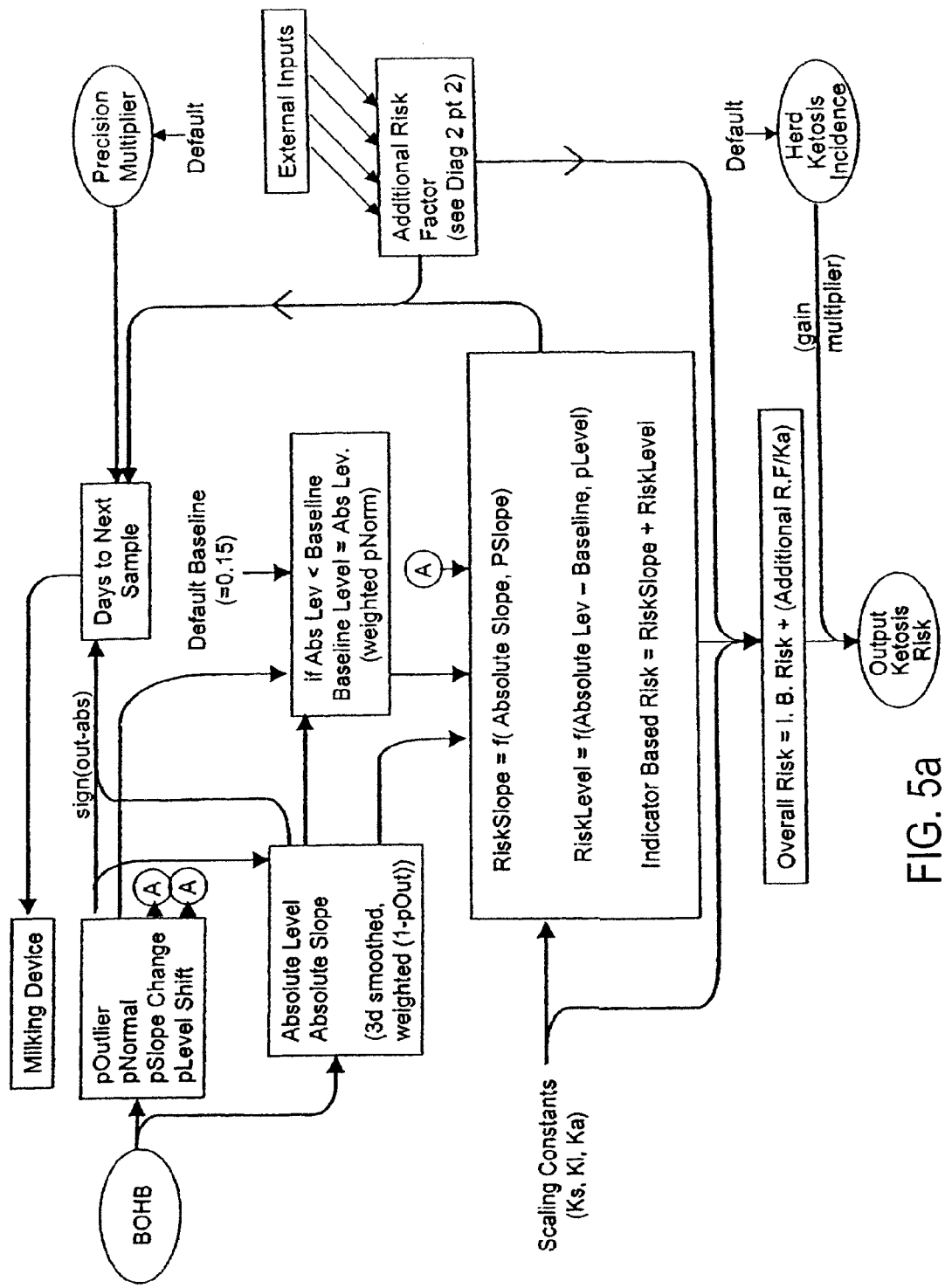
FIGS. 5a and 5b show information flow according to an embodiment of the present invention when analysing for BHB and ketosis.
Figure 5B:
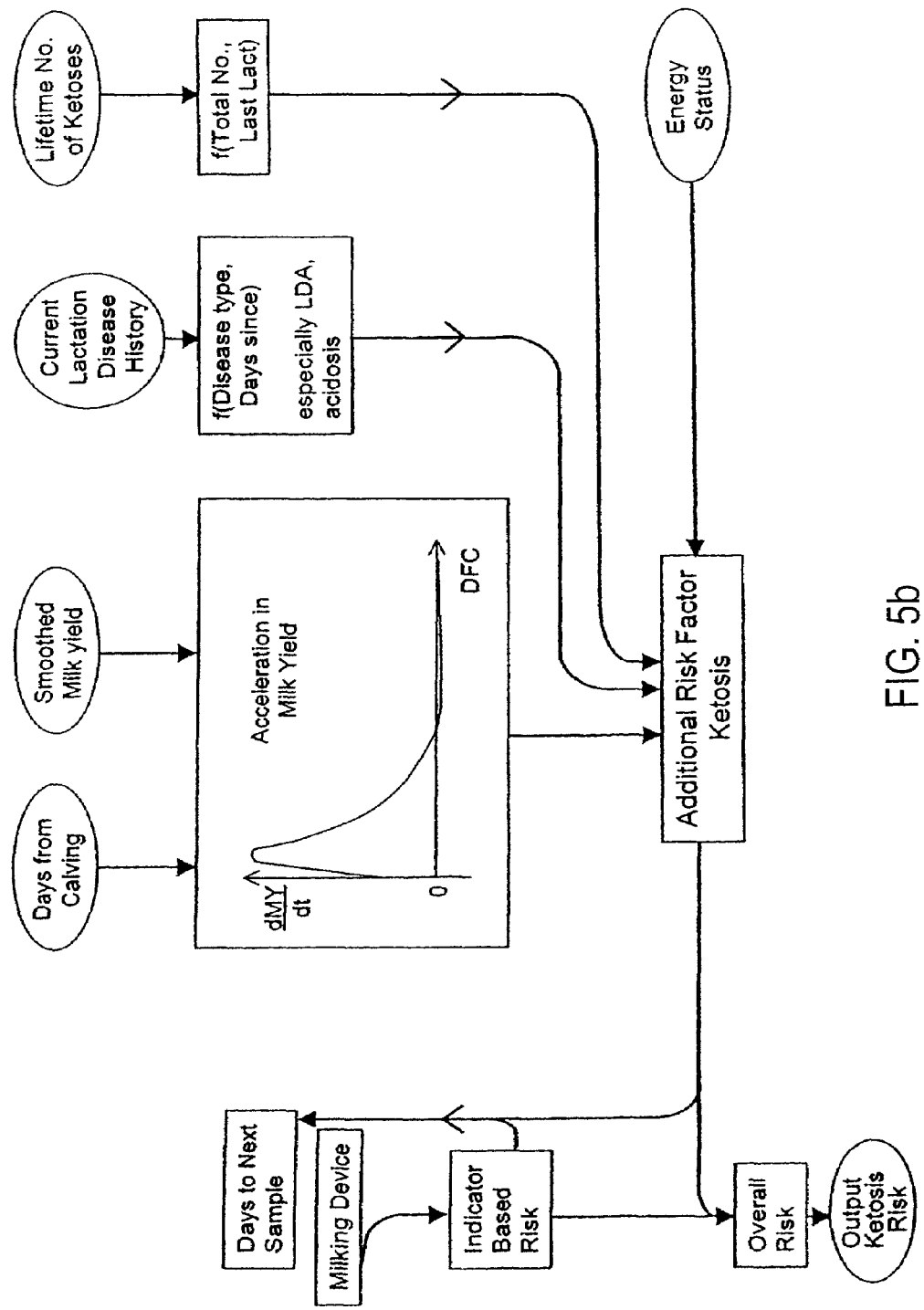

Application of the Present Invention for the Determination of BHB and Ketosis:

In another preferred embodiment of the present invention subclinical and clinical ketosis and BHB in e.g. milk is detected in a manner which, as shown in FIGS. 5a and 5b. In this system the baseline levels of BHB are expected to be substantially lower than the values found with ketosis. Further, after a ketosis incident values will return to the original baseline. The rate of onset of ketosis is such that we anticipate using a 3 day smoothed value to calculate risk. It is important to note that the bandwidth chosen for smoothing is time and not number of samples i.e., if only one sample was taken in the 3 preceding days then the smoothed value contains only that one measurement. This applies to all bandwidths in these models.

The basis for the ketosis model is the ketone body: beta-hydroxybutyrate (BHB), which has a strong relationship to clinical ketosis. The BHB measurements are used to generate an Indicator Based Risk (IBR) and an Additional Risk based on other Factors (ARF) is also generated. Together these are used to generate an overall risk of ketosis. FIGS. 5a and 5b describe the ketosis model: one describing the indicator based risk (IBR, see FIG. 5a) and another describing the additional risk factors (ARF, see FIG. 5b).

Note: All the ketosis model parameter names end with a capital K (for Ketosis), drop the ending 'K' and they should be (to some degree) readable.

Unifying Components (Days to Next Sample, Output Risk and Output Reliability)

Overall Ketosis Risk (OverRiskK)

The Overall Ketosis Risk (OverRiskK) is derived from the IBR and the ARFARFWK (Additional Risk Factor Weight Ketosis) is the scaling factor to weight the ARF relative to the IBR. An ARF is a factor that is not at all reflected in BHB, but still imposes a risk for the cow to get ketosis. It is therefore necessary that ARF's can cause an alarm if no BHB-measurements are available, e.g. the first days after calving where it is likely that no samples will be available.

It should also be stated that ARF is weighted against IBR, and that this weight-factor presumably will be adjusted according to the reliability of the factors that contributes to the calculations of ARF and IBR.

Days to Next Sample (DNSK)

As the biological model perceives an increased risk of ketosis so the days to next sample is reduced from a default value (DNSdefK). If a high probability comes out from IBR, ARF or there is a high probability that a measurement was an outlier (POutlierK), we are interested in getting a new sample as quick as possible.

The model calculating DNSK is then adjusted by the Precision Multiplier. The purpose of the Precision Multiplier is to allow the user to modify the general rate at which the milking device takes another sample i.e. the overall intensity of monitoring for ketosis. The Precision Multiplier works at the level of the whole model i.e., the user can adjust the sampling frequency for ketosis in general but he cannot adjust the sampling frequency for individual cows. As the name suggests, the Precision Multiplier (PrecMultK) is a simple multiplier on Days to Next Sample (DNSK).

Output Ketosis Risk (OutRiskK)

The final output risk presented to the user (OutRiskK) is generated from the overall risk (OverRiskK) multiplied by the Gain multiplier. The Gain Multiplier (GainMultK) provides the possibility of expanding or contracting the range of risk values being produced. It is envisaged as a means to adjust the model to local conditions, e.g. if in a particular region/farm it is found that the ketosis model only ever produces risk values between 0 and 0.5 even though clinical cases of ketosis are being observed, then the GainMultK could be changed. Furthermore, it follows that if GainMultK is 0, then OutRiskK=0 and therefore no cows will be pointed out with risk of ketosis in this herd.

Output Reliability (OutRelK)

The Output Reliability reflects the noisiness of the BHB signal, the sampling frequency for BHB, and the quality of the ARF information. If the user has set the milking device to take very few BHB measurements and is not entering any of the supplementary information e.g. health records, then it is desirable to let the farmer know that the risks being generated by the ketosis model are of lower reliability. The noisiness of the signal can be obtained from the posterior variance in the State Space model (SSM). This value is then multiplied by a function, which decreases from 1 to 0 with increasing interval length between the current and previous samples (IntK) to give RelIBRK. For the ARF, those factors derived from the State Space Model (SSM) (i.e. acceleration in milk yield and energy status) use the same functional form as for the SSM, while those factors which are herd management/user inputs have one value if there is information and are zero if that factor is not being supplied (the following list may make more sense after reading the section on ARF).

If all the information which goes into the ARF is perfect then RelARFK=1. The Output Reliability is then the sum of RelIBRK and RelARFK weighted in proportion to their contributions to the output risk:

Elements of the Indicator Based Risk (IBR)

The IBR is based on measurements of BHB in milk. From these, a risk due to the level of BHB and a risk due to the rate of change of BHB are calculated and combined to give IBR. The rate of change of BHB is considered an important element of the model when identifying ketosis at an early stage. Some cows have a high tolerance of ketone bodies, i.e. they have a high level of ketone bodies in the body fluids without showing clinical signs. However, these cows have been considered as risk cows even though they may not need treatment, because a relatively small increase in BHB will take them to a high BHB level.

Baseline of BHB (BaselineK)

The BaselineK is calculated for each cow and is a smoothed level of BHB (LevelK), where each BHB-value is weighted by PNormal (a probability from SSM) to account for outliers. There is a restriction in the function namely that BaselineK is less than e.g. 0.15 mM, because it is unrealistic with a natural higher baseline As soon as BHB is measured after calving the baseline will adjust itself according to the individual cow. It is expected that 0.15 mM is a relatively high maximum baseline, which is useful in most herds and countries, but the maximum baseline may be adjusted in accordance with national law in a particularly country.

Risk Due to Slope of BHB (RiskSlopeK)

It is assumed that the greater the positive rate of change of BHB (SlopeK), the greater the risk is of ketosis. SlopeK is a smoothed output from SSM adjusted for PslopeK which is a probability calculated in SSM. MaxSlopeK is a constant which will give a RiskSlopeK=1. The suggested value of MaxSlopeK is 0.5 due to the assumption that BHB in severe clinical cases of ketosis/left displaced abomasum can increase from app. 0 mM to 2 mM during a 4 days period. I.e. a slope of 0.5 which when divided by MaxSlopeK (0.5) will give a RiskSlopeK=1 (if PslopeK is assumed 0). RiskSlopeK can assume values <0 and >1.

Risk Due to Level of BHB (RiskLevelK)

The higher the level of BHB (LevelK) compared to the baseline level of the individual cow (BaselineK), the greater the risk of ketosis. The use of a baseline with a maximum value of 0.15 relies on the assumption that concentrations >0.15 mM are associated with physiological imbalance that can mediate a subclinical or clinical ketosis. LevelK is a smoothed output from SSM and PLevelK is a probability calculated in SSM. MaxLevelK is a constant which will give a RiskLevelK=1. Under the assumption that a cow with 1.0 mM BHB has clinical ketosis, i.e. RiskLevelK=1, the suggested value for MaxLevelK is 1.0. RiskLevelK may assume values <0 and >1.

Indicator Based Risk (IBR)

IBR is calculated as a weighted combination of RiskSlopeK and RiskLevelK.

The Additional Risk Factor (ARF)

As mentioned earlier, the crucial point about ARF is that the ketosis risks included here are not already included in the IBR, i.e. any factor, which will affect BHB, should not be included here. In those cases where a factor has both an effect on BHB and an additional effect it is necessary to distinguish between these two effects and only include the additional effect in the ARF.

The elements that make up the ARF are described below; they combine to give ARF as follows:

Acceleration in Milk Yield

The higher maximum milk yield (kg/day), the higher risk of ketosis, in some cases 2.5% higher risk pr. kg increase in milk yield (test day milk yield used). However, it seems more likely that it is the acceleration in milk yield that is interesting in relation to the development of ketosis. It seems logical that too heavy acc. in milk yield (MYAcc) would increase the risk of a breakdown/imbalance in the fat- and carbohydrate metabolism of the cow and thereby increase the risk of ketosis. In this case MYAcc is an ARF because a high MYAcc presumably precedes a rise in BHB.

MYAcc is the slope of the milk lactation curve of the individual cow and is an output from SSM on the basis of days from calving and daily milk yield recordings. MaxAccK is a scaling constant, which defines the level of MYAcc that will return a RiskAccK of 1. RiskAccK can assume values above 1, in this particular embodiment all negative values of RiskAccK should be converted to 0. The suggestion for this constant in this case is 3, because this is believed to be the maximum reasonable increase in kg milk/day when it is smoothed over 3 days.

Current Lactation Disease History (CLDHRiskK)

The physiological background for the fact that other diseases often increases the risk of ketosis is, that other diseases can induce a decreased feed intake that can lead to an increased mobilization. Depending on the duration and the volume of this mobilization and the capacity of the liver to fully oxidize this fat from the adipose tissues the cow can develop subclinical or clinical ketosis. Choosing the diseases that could cause ketosis (and therefore should be included in the model) is among other things based on epidemiological investigations, which are briefly presented in the following section:

The risk of ketosis was increased by e.g. milk fever. Studies have shown that metritis significantly increases the risk of getting ketosis, while ketosis significantly increases the risk of LDA. The development of LDA is shown clearly to associate with high ketone levels and could be assumed bidirectional. But no studies have shown the effect (Odd ratio: OR) of LDA on ketosis has been estimated. Furthermore, studies have shown a significant effect of mastitis on ketosis where there were found different results depending on the definition of mastitis: OR=1,4 (1,2-1,7) for acute mastitis and OR=2,4 (1,7-3,3) for chronic mastitis. This could imply that different types of mastitis (bacteriatypes) have different effects on the risk of getting ketosis. Furthermore, a reason for discrepancies between studies could be a difference in the distribution of mastitis in relation to calving date. Mastitis does not seem to affect the risk of getting ketosis.

A function is used to calculate the risk of ketosis due to a given disease (DisRiskK) as a function of days since occurrence (DisDaysK), an expected risk period, i.e. the day where the disease no longer is believed to be a risk for ketoisis (DisTK) and the severity of the disease (DisSevK).

In table 2 different diseases are listed according to their suggested maximum risk (MaxDisK). DisRatK determines the shape of the curve between MaxDisK and DisTK, i.e. how DisRiskK changes from the day of treatment until the risk period has expired. DisTK gives the number of days until the risk has reduced to 0.36 (exp(−1) or 1/e).

TABLE 1

List of diseases according to their maximum risk.

| Disease (DisTypeK) | MaxDisK | DisTK (days) | DisRatK |
|---|---|---|---|
| LDA (left displaced abomasum) | 0.9 | 10 | 0.4 |
| RDA (right displaced abomasums) | 1.1 | 10 | 0.4 |
| Rumen Acidosis | 0.7 | 10 | 0.4 |
| Milk fever | 0.6 | 8 | 0.4 |
| Retained placenta | 0.3 | 12 | 0.15 |
| Metritis | 0.5 | 12 | 0.15 |
| Mastitis | 0.2 | 8 | 0.4 |
| Other | 0 | 0 | 0 |

Diseases can not be considered totally independent and therefore it could lead to overestimation of the ARF, if the risk of each disease is added together in a cow that experiences several diseases at the same time (e.g. mastitis and metritis). Therefore, it is always the disease with the highest risk factor at the given day that counts in the calculation of the total ARF. If a cow has experienced repeatedly treatment of the same disease within a lactation, then only the last incidence of this particular disease should count in the calculation of DisRiskK. Thus, it is necessary that DisRiskK is calculated every day for each of the last incidences of the diseases in the current lactation.

Lifetime Number of Ketosis

The background for including a cow's history of ketosis is the following facts: there is approximately 2.5 times higher risk of getting ketosis if the cow had ketosis in the previous lactation. Estimates shows that cows treated for ketosis in the first lactation have a 17% risk of ketosis in the second lactation, while those that were not treated in the first lactation have a 4% chance of ketosis in the second lactation. The equivalent values have been shown to be 8 and 3% and a cow with milk fever in a previous lactation has 2-5 times higher odds of milk fever and a cow with ketosis in a previous lactation has 4-12 times higher risk of getting ketosis again.

The ARF due to earlier incidences of ketosis is assumed constant during lactation because it expresses a constant susceptibility or different sensitivity between cows. Therefore, it is considered a genetic factor. The additional risk from earlier incidences of ketosis may be included via a constant for the cows history (HistConK). The constant is depending on the history of ketosis Energy Status (EnStat)

In the situation where the nutritional environment is limiting, excessive mobilisation of body energy reserves may occur putting pressure on the cow's physiological balance. Energy Status is a measure of this, it is also the output of the Energy Status Model. It is expected that poor energy status will increase the risk of ketosis. This Energy Status may be included as an ARF.

List of Inputs and Outputs

Suggested Inputs

| Parameter | Comment |
|---|---|
| CowID | Unique ID, duplicates not allowed |
| RunTimeK | Date and time of the current run |

-continued

| Parameter | Comment |
|---|---|
| BHBTimeK | Date and time of the latest BHB sample |
| GainMultK | Gain Multiplier - input for adjusting to local conditions |
| PrecMultK | Precision Multiplier - input for adjusting to local conditions |
| LevelK | Concentration of BHB - smoothed output of SSM |
| SlopeK | Rate of change in BHB - smoothed output of SSM |
| IntK | Time interval between the latest and the previous BHB samples |
| POutlierK* | Probability value from SSM |
| PNormalK* | Probability value from SSM |
| PSlopeK* | Probability value from SSM |
| PLevelK* | Probability value from SSM |
| DisDateK | Date and time of disease |
| DisTypeK | Code for different diseases# |
| DisSevK | Codes: possible = 0.3, probable = 0.6, definite = 0.9 |
| DFC | Days From Calving - should be validated against prior pregnancy and AI records. |
| MYAcc | Slope of the milk lactation curve - smoothed output of SSM based on daily milk yield recordings and DFC from Herd Man. Sys. |
| EnStat | Energy status, output of another model |

*Must be available both as estimates to time t and one step back-smoothed the prior estimate (t − 1).
Left displaced abomasum, right displaced abomasums, rumen acidosis, milk fever, retained placenta, metritis, mastitis, ketosis and other.

Synchronicity of Inputs

The model is built on the basis that a new BHB-value triggers the model to run. Furthermore, a new sample/calculation may also be triggered when a disease is entered, i.e. when DisDateK is input.

Suggested Outputs to the End-user

| Parameter | End-User | Comment |
|---|---|---|
| DNSK | Milking device | Days to next sampling |
| OutRiskK | Cow Manager | Output Risk of Ketosis |
| OutRelK | Cow Manager | Reliability of Output Risk of Ketosis |

Figure 6A:
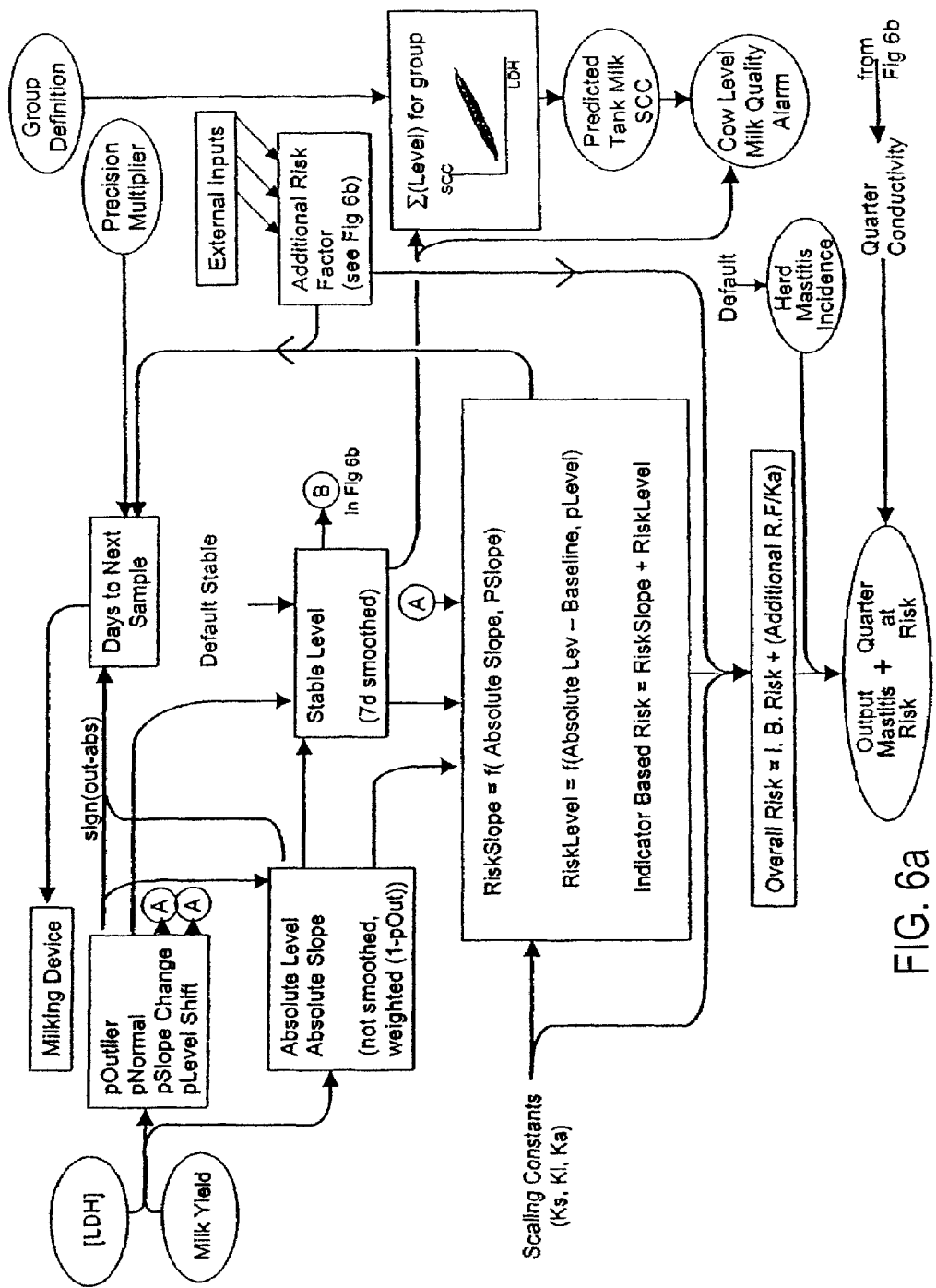
FIGS. 6a and 6b show information flow according to an embodiment of the present invention when analysing for mastitis indicators (e.g. NAGase or LDH) and mastitis.
Figure 6B:
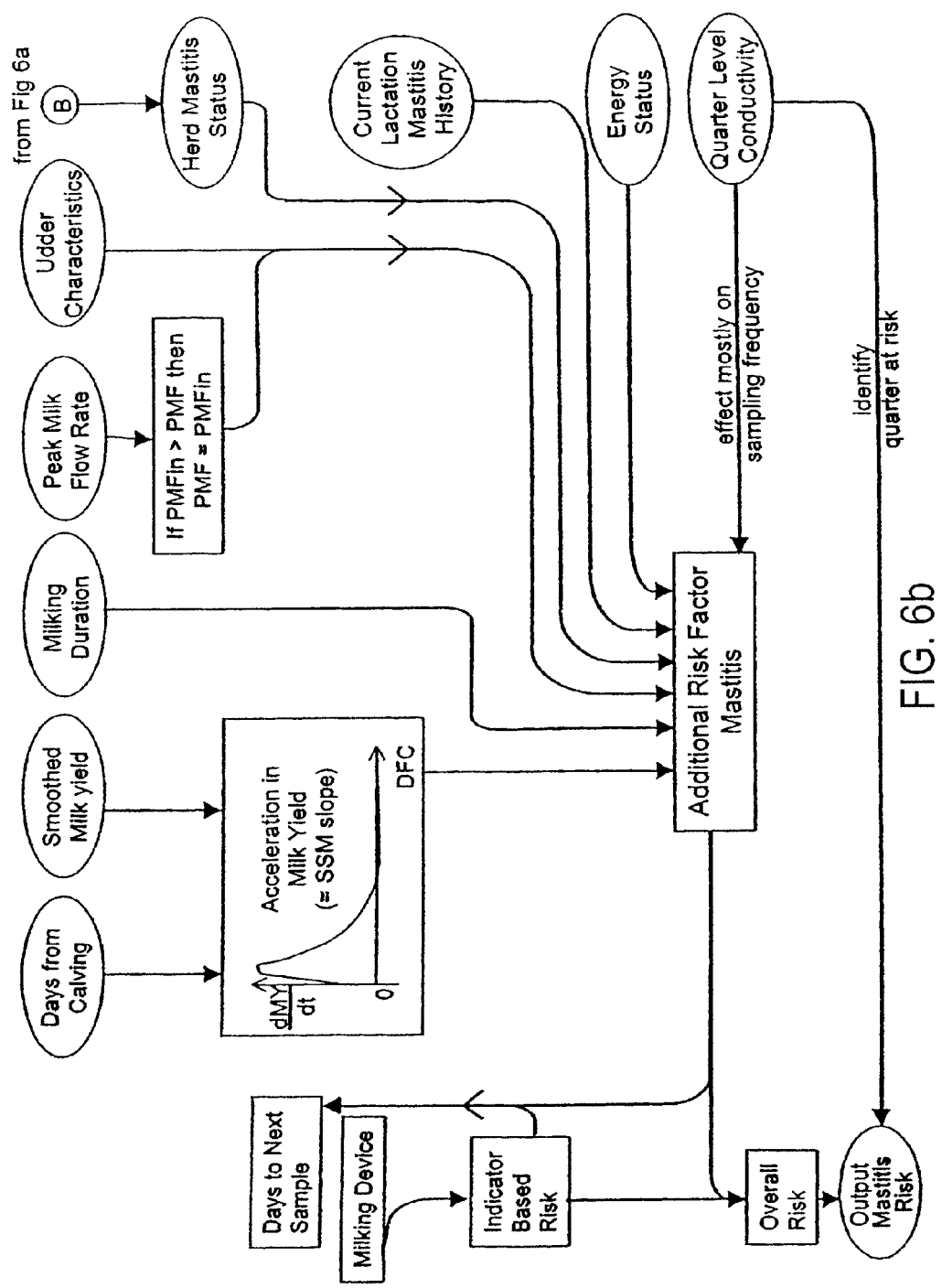

Application of the Present Invention for the Determination of Mastitis:

Matitis Indicators may be e.g. LDH or NAGase. In yet a preferred embodiment of the present invention Mastitis Indicators and mastitis is detected in animals, as shown in FIGS. 6a and 6b. There are many similarities between the mastitis model and the ketosis model. There are two major differences from the ketosis model. The first is that the baseline Mastitis Indicator level does not necessarily return to pre-infection levels. The second is that there are some population or group level milk quality requirements.

Note: All the mastitis model parameter names end with a capital M (for mastitis), drop the 'M' and they should be (to some degree) readable.

Model Basis

The basis for the mastitis model may be lactate dehydrogenase (LDH) which in this embodiment of the present invention is selected for illustrative purposes only. It is assumed that there is a strong linear relationship between LDH and udder health status. The LDH measurements are used to generate an Indicator Based Risk (IBR), an Additional Risk based on other Factors (ARF) is also generated. Together these are used to generate an overall risk of mastitis. The structure of the model is shown in FIGS. 6a and 6b.

An important issue concerns the effects of dilution. Assuming that LDH is produced in response to an amount of milk cell damage then the amount of LDH may be a more relevant indicator of mastitis than the concentration of LDH in the milk. Clearly, if this is the case then the concentration of LDH which constitutes a mastitis alarm will be dependent on milk yield. In addition, mastitis usually occurs in only one quarter at a time and the milk from that quarter is diluted by milk in the other three quarters. A further complication is that the ratio of milk amounts produced by the infected and healthy quarters is also affected by mastitis. Consequently, it may be decided to use LDH amount and not LDH concentration as the indicator variable in the biological model. This amount (LDH) is the input to the biological model, it is generated from the LDH concentration (LDHconc) and milk yield at that milking (MY).

Dealing with Acute Cases Versus Chronic Cases of Mastitis

Acute cases of mastitis are characterised by a sudden rise in the level of the mastitis indicator i.e., LDH, whereas chronic cases are typified by a high and relatively stable level of LDH. The architecture of the mastitis model for identifying acute cases is very similar to the general model structure FIG. 4 and to the model for ketosis in particular FIGS. 5a and 5b. These acute cases should generate a high Risk of Mastitis.

Chronic cases will not necessarily feature in the Risk of Mastitis but will instead generate a high value in the Milk Quality Risk. This "milk quality" module of the mastitis model is based on the stable level of LDH relative to the herd average. The key to distinguishing between acute and chronic mastitis is in the calculation and use of the stable level.

Unifying Components (Days to Next Sample, Output Mastitis Risk and Output Reliability)

Days to Next Sample (DNSM)

As the biological model perceives an increased risk of (acute) mastitis so the days to next sample is reduced from a default value (DNSdefM). In addition to the effects of a high indicator based risk (IBR) or additional risk factor (ARF), if the latest LDH value has a high probability that it is a positive deviation from the normal time series then another sample is taken quickly. Also, if there is a high conductivity measurement (CondM) a follow-up sample is quickly taken.

The model calculated DNSM is then adjusted by the Precision Multiplier. The purpose of the Precision Multiplier is to allow the user to modify the general rate at which the milking device takes another sample i.e. the overall intensity of monitoring for mastitis. As the name suggests, the Precision Multiplier (PrecMultM) is a simple multiplier on Days to Next Sample (DNSM).

Output Mastitis Risk (OutRiskM)

The Mastitis Risk presented to the user (OutRiskM) is generated from the Overall Mastitis Risk (OverRiskM), which is derived from the IBR and the ARF.

IBR is the indicator based risk and ARF is the risk due to the additional risk factors. The final output risk (OutRiskM) is calculated from the overall risk by applying a multiplier, the Gain Multiplier. The gain multiplier provides the possibility of expanding or contracting the range of risk values being produced. It is envisaged as a means to adjust the model to local conditions, e.g. if in a particular region/farm it is found that the mastitis model only ever produces risk values between 0 and 0.5 even though clinical mastitis cases are being observed, then the Gain Multiplier could be changed. The wisdom of doing this and who should be given the access privilege remains to clarified.

Output Reliability

The Output Reliability reflects the noisiness of the LDH signal, the sampling frequency for LDH, and the quality of the ARF information. If the user has set the milking device to take very few LDH measurements and is not entering any of the supplementary Information e.g. health records, then it is desirable to let the farmer know that the risks being generated by the mastitis model are of very low reliability. The noisiness of the signal can be obtained from the posterior variance in the SSM. This value is then multiplied by a function which decreases from 1 to 0 with increasing interval length between the current and previous samples (IntM) to give RelIBRM. For the ARF, those factors derived from SSM use the same functional form as for RelIBRM, while those factors which are herd management/user inputs have one value if there is information and are zero if that factor is not being supplied (table 4 indicates the reliability of different types of measurements:

TABLE 2

Indicates the reliability of different types of measurements.

| Name | Abbreviation | Reliability |
|---|---|---|
| Acceleration in milk yield | RelMYAccM | post. var. function with maximum = 0.4 |
| Milking Duration | RelMilkDurM | post. var. function with maximum = 0.1 |
| Peak Milk Flow | RelPMFM | post. var. function with maximum = 0.05 |
| Udder Characteristics | RelUddM | maximum = 0.2, 0 if missing |
| Herd Mastitis Level | | Not included in reliability |
| Current Lactation Disease | RelCLDHM | maximum = 0.15, 0 if missing |
| Energy Status | RelEnStatM | post. var. function with maximum = 0.1 |
| Conductivity | | Not included in reliability |

If all the information which goes into the ARF is perfect then RelARFM=1. The Output Reliability is then the sum of RelIBRM and RelARFM weighted in proportion to their 2 contributions to the output risk.

Elements of the Indicator Based Risk (IBR)

The Indicator Based Risk is simply the sum of two risks; the risk due to the level of LDH and the risk due to the rate of change in LDH level. These and the associated elements are detailed below.

Stable Level (StableM)

This is basically, for each cow, an average value of the LDH level (LevelM) calculated over a time interval such as 7 days (StableIntM). As LevelM already accounts for the probabilities of being a normal value etc, there is no further need to account for this in the calculation of the stable level (StableM).

A default value of StableM might be needed at calving for the calculation of the risk due to LevelM, this should be set low and be diluted out as actual LevelM data accumulates.

Risk Due to Slope (RiskSlopeM)

It is assumed that the greater the rate of change of LDH (SlopeM), the greater the risk of mastitis. RiskSlopeM is increased if there is a high probability that it is a deviation from the normal time series, i.e. a slope change (PSlopeM).

Risk Due to LDH Level (LevelM)

It is assumed that the higher the level relative to the stable level (StableM), the greater the risk of mastitis. The use of the stable level as a baseline facilitates the differentiation between acute and chronic mastitis but it also relies on the assumption that the increase in LDH due to an acute case is independent of the underlying stable level. If this is not the case, for instance if the level of LDH associated with a "full-blown" mastitis is absolute, then the model will need to use a different baseline, such as that used in the ketosis model.

The Additional Risk Factor (ARF)

The crucial point about the Additional Risk Factor is that the mastitis risks included here are not already included in the Indicator Based Risk i.e. any factor which will affect LDH should not be included here. In those cases where a factor has both an effect on LDH and an additional effect it is necessary to distinguish between these two effects and only include the additional effect in the ARF. The elements that make up the ARF are described below, they combine to give ARF Acceleration in Milk Yield (MYAcc)

This is used as an index of the degree of physiological stress that the cow is experiencing. MYAcc is a way of combining milk yield and days from calving which we believe crystallises the components of these two factors which are relevant to the physiological stress being experienced by the cow. MYAcc is highest immediately after calving and is higher for higher yielding cows.

Given that there is a biometric model for milk yield then, in principle, the slope of the smoothed milk yield curve i.e., acceleration in milk yield, is readily available. Additionally, MaxAccM is a scaling constant is needed to give the level of acceleration which will return a risk of 1.

Duration of Milking

This is assumed to index the negative physical effect of machine milking on the cow's teat defenses to invasion by mastitis causing pathogens. The longer the duration of milking (MilkDurM), beyond some lower threshold, the greater the effect.

Udder Characteristics

The quantification of the cow's own susceptibility to mastitis is in 2 parts; that information which is categorical (generally input by the user), and that which is on a continuous scale. These are essentially risk factors which are not expected to change on a short timescale. The categorical udder characteristics are currently:

TABLE 3

Udder characteristics

| Udder Characteristic | Name | Increase in risk |
|---|---|---|
| Short teats | ShortM | 0.1 |
| Low udder | LowM | 0.05 |
| Leaky teats | LeakyM | 0.15 |

Peak Milk Flow Rate and Lifetime Number of Mastites

The continuous factors may be peak milk flow rate and lifetime number of mastitis. Peak milk flow rate (MilkFlowM) should be available from the milking system at each milking where a sample is taken. In the present context, peak milk flow rate is an index for teat canal diameter, this does not change markedly through lactation. However, peak milk flow rate itself is affected by milk yield because the pressure created in the udder by the alveolar contraction during the milk ejection reflex will depend on how full the udder is. Thus, this could be measured at a particular stage of lactation or yield. One way of approximating this is to use the maximum recorded peak milk flow rate. As this routine is vulnerable to noisy measurements, the input peak milk flow rate should be the output of an SSM. The peak milk flow rate (PeakMFM) is converted to a risk factor.

The lifetime number of mastites could be used as a measure of the cow's susceptibility to mastitis in the same way that the lifetime number of ketoses is used in the ketosis model. However, there is a crucial difference in that mastitis is an infectious disease and ketosis is not. Thus, to some extent we can expect the lifetime number of mastites to reflect the disease pressure placed on the cow by the environments she has been in. For this reason this is not considered being a variable of choice as a predictor of the cow's susceptibility but it has the practical advantage of being automatically generated if the risk of mastitis output is used to generate disease incidences.

Herd Mastitis Level

Given that mastitis is an infection, the more mastitic cows in the herd, the higher the infection pressure on any given cow in the herd. The Herd Mastitis Level can be calculated by combining the individual infection burdens of the cows in the herd which are assumed to be reflected in the stable LDH amounts (StableM).

Current Lactation Disease History (CLDHRiskM)

This is analogous to the same factor in the ketosis model except that the distinction is made between diseases that indicate increased infection burden (metritis, teat tramp, acidosis) and those which just add to the general stress the cow is experiencing ketosis, milk fever, retained placenta and other. For each of these, there is an increased risk of mastitis on the day of occurrence that then decays to zero over time.

At any one time, there may be more than 1 disease risk in operation, these are combined in the following way. Within each class of disease (infection vs general) the greatest DisRiskM is chosen i.e. it is assumed that within class risks are not additive. The overall current lactation disease history risk (CLDHRiskM) is the sum of two DisRiskMs, the highest within each class.

Energy Status (EnStat)

In the situation where the nutritional environment is limiting, excessive mobilisation of body energy reserves may occur putting pressure on the cow's physiological balance. Energy Status is a measure of this, it is also the output of the Energy Status Model. It is expected that poor energy status will increase the risk of mastitis (among others). Thus, Energy Status is included as an ARF.

Quarter Level Conductivity

Conductivity has 3 advantages as a measure; it is very cheap, very quick, and at quarter level. These advantages should be taken advantage of when the milking system has conductivity. However, it is assumed that LDH is the more reliable indicator. Therefore the risk due to conductivity (RiskCondM) is given a relatively low weight in the ARF The 2 most important roles of the conductivity input are to trigger a new sample and to identify which quarter is mostly likely infected.

Milk Quality Risk—Dealing with Chronic Mastitis Cases

In it's simple form this could just be an output list of individual StableM values. By using a correlation between LDH and SCC it is possible to predict bulk milk SCC and thus judge whether any cows should have their milk withheld from the bulk tank.

List of Inputs and Outputs

Suggested Inputs

| Parameter | Comment |
|---|---|
| CowID | Unique ID, duplicates not allowed |
| RunTimeM | Date and time of the current run |

-continued

| Parameter | Comment |
| --- | --- |
| LDHTimeM | Date and time of the latest LDH sample |
| LevelM* | LDH amount - smoothed output of SSM |
| SlopeM* | rate of change in LDH amount - smoothed output of SSM |
| IntM | Time interval between the latest and the previous LDH samples |
| POutlierM* | probability values from SSM |
| PNormalM* | probability values from SSM |
| PSlopeM* | probability values from SSM |
| PLevelM* | probability values from SSM |
| CondtimeM | Date and time of a conductivity measurement |
| CondM | Conductivity alarm value - a value between 0 and 1 |
| QuarterM | The quarter which the conductivity alarm is detecting |
| PMM | Precision Multiplier for mastitis |
| DFC | Days from Calving - should be validated against prior pregnancy and AI records. |
| MYAcc | Slope from the SSM on milk yield (kg/d/d) |
| MilkDurM | Duration of milking (s) |
| UdderM | Udder characteristics eg. leaky teats see eqn 9 for the full list |
| PeakMFM | $Level_{t-1}$ from an SSM on peak milk flow rate |
| DisTypeM | Code for type of disease type# |
| DisDateM | Date of first identification of disease |
| DisSevM | Code for severity of disease: mild = 0.3, average = 0.6, severe = 0.9 |
| EnStat | Energy status, output of another model |
| GainMultM | Gain multiplier. privileged access input for adjusting to local conditions |

*Must be available both as estimates to time t and one step back-smoothed, the prior estimate (t − 1).
Metritis, teat injury, acidosis, ketosis, milk fever, retained placenta, and other.

Suggested Outputs to the End-user:

| Parameter | Comment |
| --- | --- |
| DNSM | Days to next sampling |
| OutRiskM | Output risk for acute mastitis |
| QuarterM | Quarter at risk |
| ReliabilityM | Reliability of output risk |
| StableM | stable level of LDH - indicator of chronic mastitis |
| BulkSCCM | herd mean stable level - adjusted |

Application of the Present Invention for the Determination of Progesterone and Reproduction:

In another preferred embodiment of the present invention reproduction and progesterone is detected in animals, as shown in FIGS. 7a-7d. This model is in structure more complicated than the models for ketosis and mastitis because it may be of interest that a larger number of conditions may be identified. After calving, the cow progresses through 3 reproductive states in sequence; postpartum anoestrus, oestrus cycling, pregnant. These are referred to as status 0, 1, and 2 respectively. During the postpartum anoestrus progesterone levels are low, the end of this phase is characterised by the first, usually silent, oestrus. Detection of the first oestrus changes status to 1. Status is changed to 2 after artificial insemination. If the cow is found to not be pregnant then status reverts to 1.

Figure 7A:
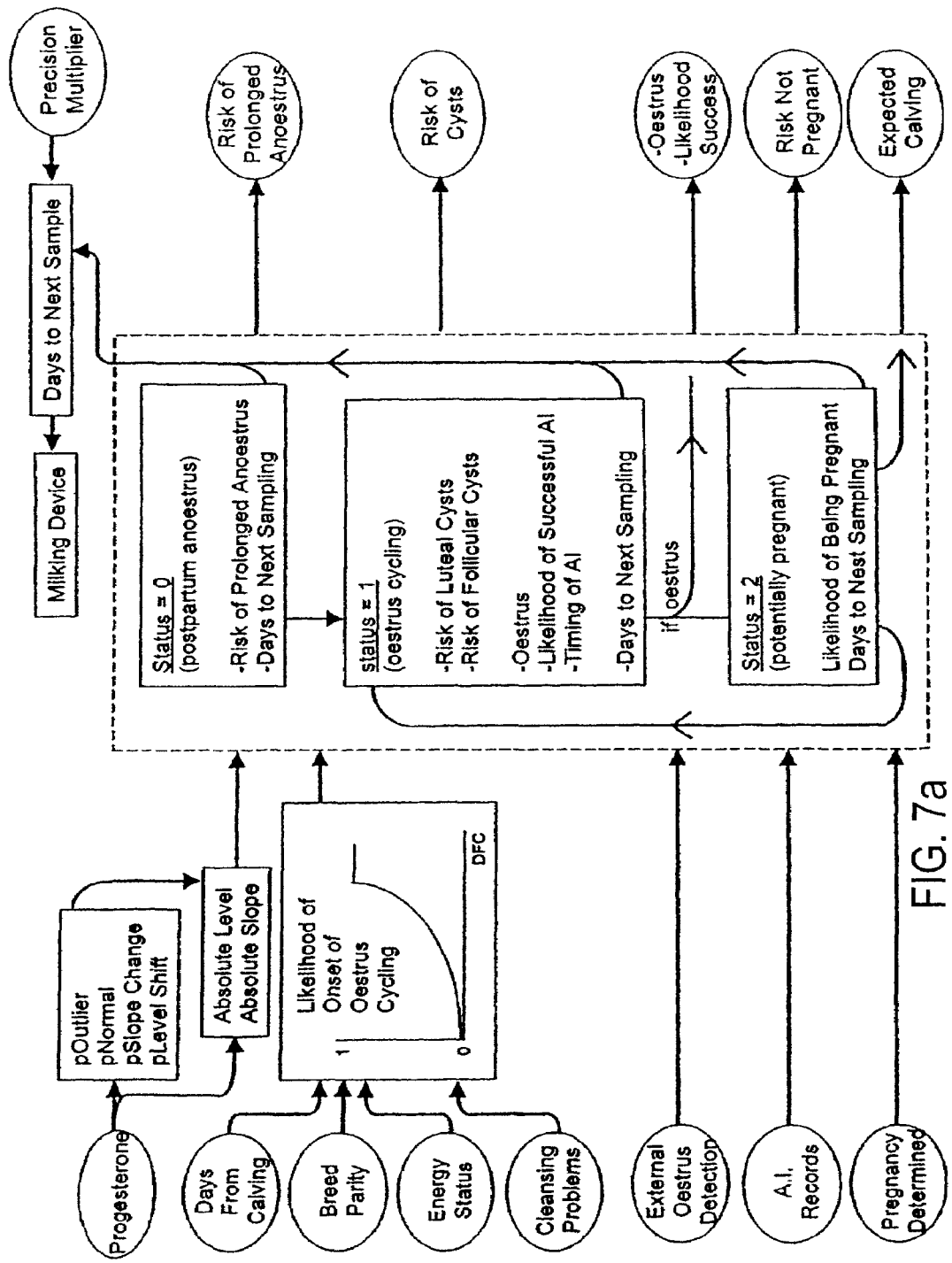

Within each state the progesterone profile may be used to indicate both normal and abnormal progressions. These are (status shown in parenthesis); prolonged anoestrus (0), luteal 'cysts' (1), follicular 'cysts' (1), pregnancy loss (2). FIG. 7a gives the overall model architecture, the decision cascade needed to identify the different conditions is shown in the stipled box. An expanded structure of this cascade is described in FIGS. 7b-7d for each of the three states, respectively.

Figure 7C:
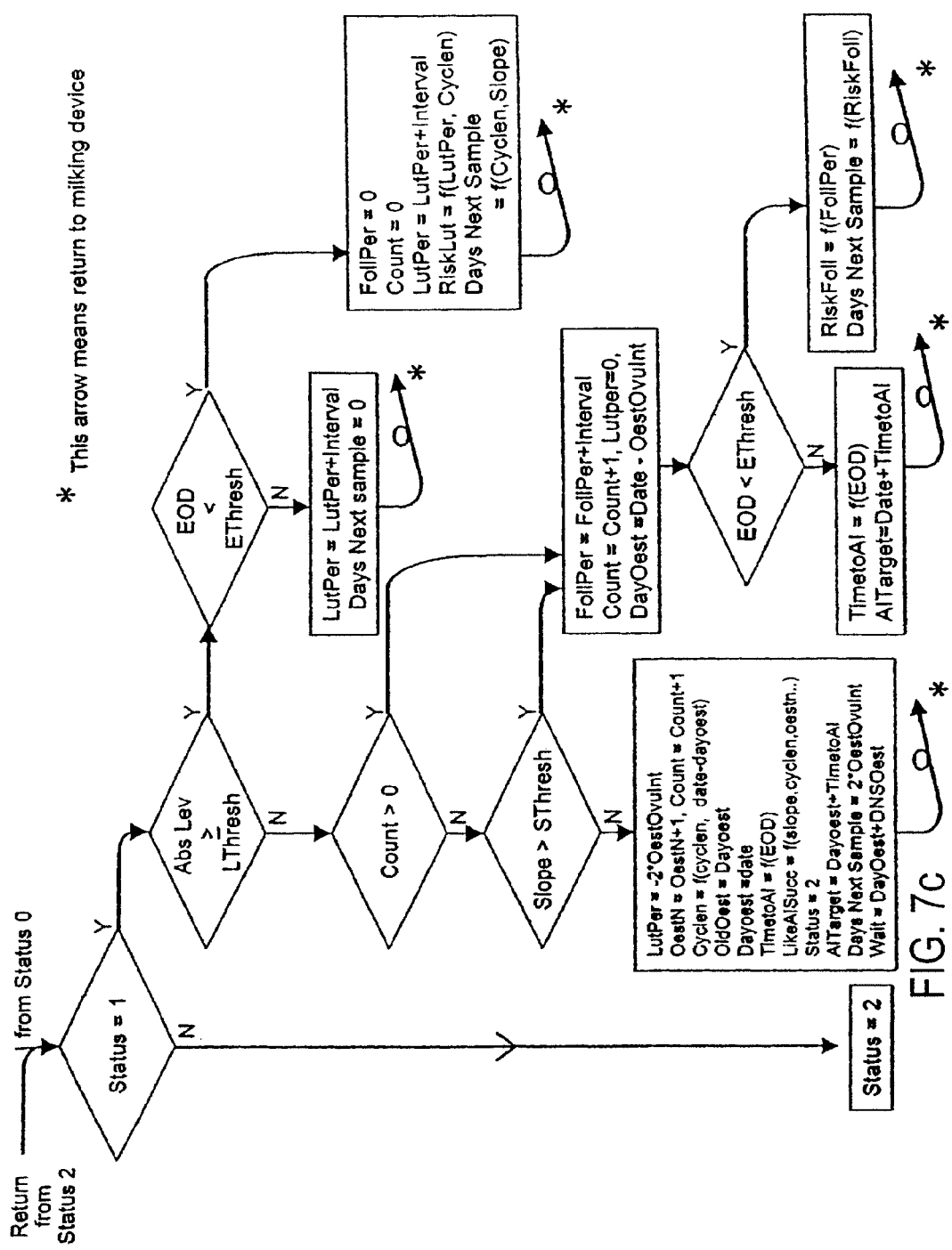
Figure 7D:
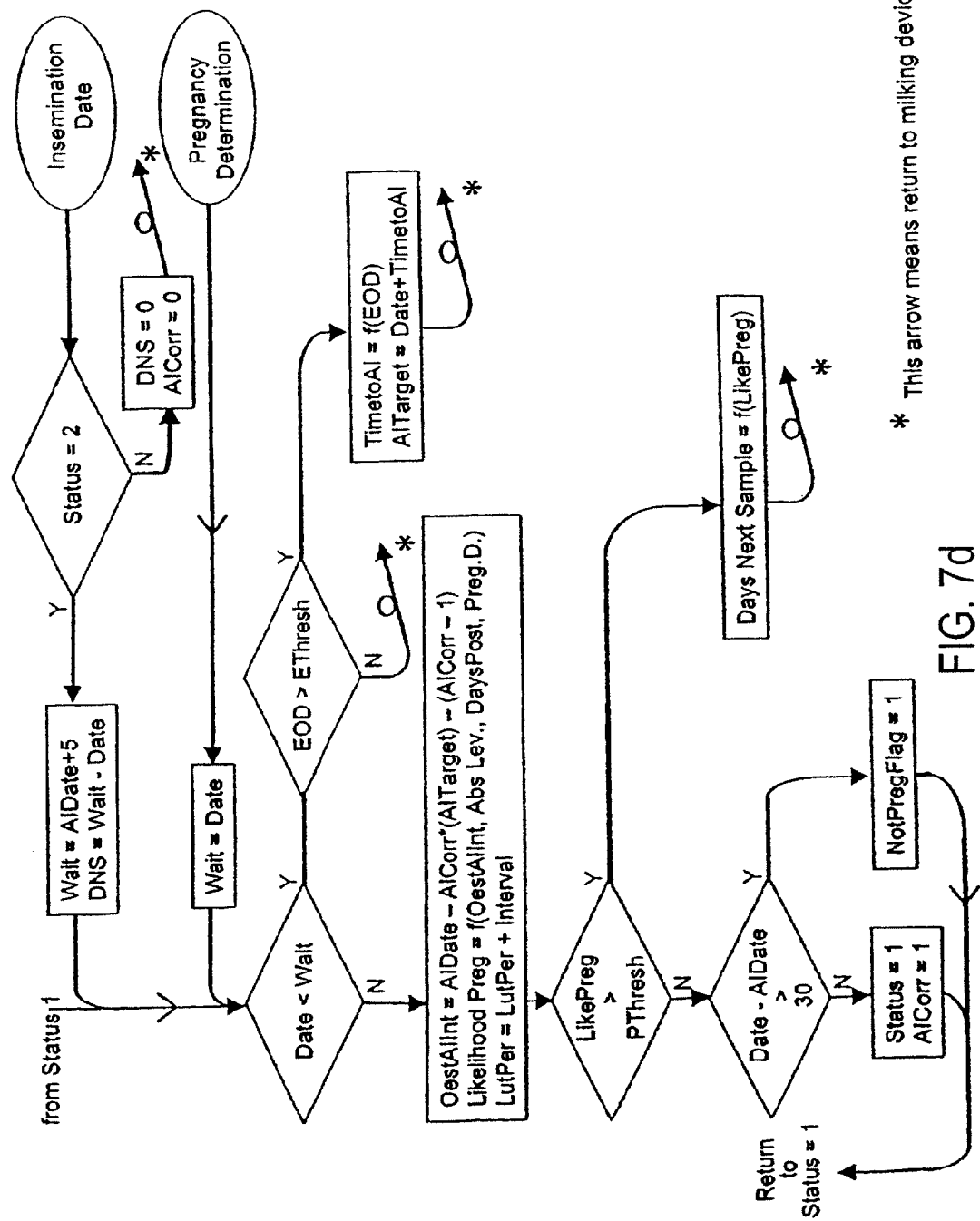

The framework for the reproduction model is based on the cow always being in one of three reproductive states (StatusR), these are:
StatusR=0 Postpartum anoestrus, (FIG. 7b)
StatusR=1 Oestrus cycling with a very low likelihood of pregnancy, (FIG. 7c)
StatusR=2 Potentially pregnant, (FIG. 7d)

In the model these states are mutually exclusive. The definition of each reproductive Status, the inputs, outputs and assumptions associated with each Status are described in detail below. A general assumption that applies to the whole reproduction model is that progesterone is the definitive measure of reproductive status. This means that although other information, such as external oestrus detections (EODR), is used it is never allowed to override the information provided by progesterone. In the terms of the general model design, progesterone equates with the "indicator based risk", EODR and other factors such as energy status equate with the "additional risk factors" (see the model overview in FIG. 7a). However, because the model has the 3 StatusR subunits it is not so easy to hold on to the IBR—ARF structure. Although it is not obvious within the biological model structure, the SSM for progesterone is important. This is evident when one considers that expected progesterone values in the follicular phase may range from 0 to 3.5 ng/ml and in the luteal phase to range from 4.5 to 50 ng/ml (mean 15-20).

Note: All the reproduction model parameter names end with a capital R (for reproduction)—drop the 'R' and they should be (to some degree) readable.

Triggering a Run of the Model and Handling Time

The model is triggered either by a new progesterone value or by an external oestrus detection. In either case, the preceding value of the other is made available. This complicates the use of time in the model.

External Oestrus Detection

Indications of oestrus behaviour are derived from external oestrus detection methods (EODR). EODR refers to all other i.e., non-progesterone, oestrus detection methods or devices. In order for the model to interface with the multitude of devices available the EOD inputs are defined as follows:

| | |
| --- | --- |
| EODTimeR = | The date and time of the external oestrus detection. This may differ from the time at which this information becomes available to the biological model, both because the run may have been triggered by a new progesterone value and because EOD values may not be real-time inputs (eg. visual oestrus detection records). |
| EODinR = | the strength, or likelihood, of the oestrus detected—on a scale from 0 to 1—supplied by the herd management system. For visual oestrus detection it is envisaged that the farmer would be able to choose between "possible", "probable" and "definite" oestrus. These would correspond to EODinR values of eg. 0.5, 0.7 and 0.9. |
| EODTypeR = | defines the type of device used for the detection. This is used to assign a decay rate to the EODinR value i.e. how much weight should I give to an EOD signal that is, for instance, a day old? For each EODType, there are 3 constants; EODRatR, EODTR, and EODgainR. This latter constant allows us to adjust original oestrus strength (EODinR) internally should this be necessary. |

EODR may then be calculated from these inputs to decline with time between current run time and EODtimeR. There might also be included a process for accumulating repeat EODs. The logic for this is that repeated evidence of behavioural oestrus should strengthen the "diagnosis" of oestrus.

StatusR=0 Postpartum Anoestrus (FIG. 7b)

This is the period from calving up to the first oestrus which then causes a subsequent rise in progesterone above the lower progesterone threshold (LThreshR). A key assumption for the functioning of the model is that the precision of the progesterone signal entering the biological model is such that real differences in progesterone between the baseline anoestrus and the threshold (LThreshR) levels are distinguishable from measurement error.

At calving, or when first registered by the model (for cows that don't start at calving), a cow is assigned Status 0. In order to progress to Status 1 evidence of a first oestrus is required. This can be either an increase in progesterone or a very strong indication of oestrus behaviour. This latter means an EODR value greater than the EOD threshold (EThreshR). It is not expected that the transition from Status 0 to Status 1 will be triggered by an EOD. However, it is included on the basis that the types of first oestrus likely to be strong enough to cause a high enough EOD would be relatively late first oestruses i.e. potentially valuable and thus (possibly) worth inseminating to.

The most likely trigger for the transition to status 1 should be the first rise in progesterone to a level higher than LThreshR. As this is an important anchor point for subsequent sampling frequency and reproductive statistics the farmer must be sure that the sample or the measurement is not just an outlier. Therefore, two consecutive progesterone values above LThreshR will likely be required to cause the shift to Status 1.

If the cow remains in Status 0 (i.e. no evidence of onset of oestrus cycling) then the risk of prolonged anoestrus (ProAnOestR) and days to next sample (DNSR) may be calculated from the EODR value and the Likelihood of Onset of Oestrus Cycling (LOOCR). LOOCR is an estimate of the biologically expected length of postpartum anoestrus. The basic idea of LOOC is that the longer from time since calving the greater the likelihood of the onset of oestrus cycling. The likelihood increases from 0 to a maximum (PropCanR) that reflects the fact that there will always be a proportion of cows which, due to reproductive malfunction, never start cycling.

The whole curve may be shifted "horizontally" by a breed factor (BreedLOOCTR) and by energy status (EnStat). In other words, the average curve for the breed-parity is now adjusted for that particular cows' energy status (a calculation from another model). In a similar way, the "slope" of the LOOCR function may be modified by individual reproductive health problems according to their type (ProbTypeR) and severity (ProbSevR). The risk of prolonged postpartum anoestrus (ProAnRiskR) is simply LOOCR adjusted down for any evidence of EOD activity. Cows with a high risk of prolonged postpartum anoestrus are those for which no good biological explanation can be found for the anoestrus—because LOOCR is adjusted for individual cow's biological modifiers of the anoestrus period. Days to next sample (DNSR) is calculated in a similar way so that a default DNS (DNSOdefR) is decreased by; increasing EOD and also increasing risk of prolonged postpartum anoestrus. In other words, if there is any hint of oestrus activity or if there is a possible problem then we want to follow that cow more closely. DNSR is calculated at a number of places throughout the reproduction program reflecting the number of different exit points of the model back to the next sampling but in any one run only one calculation is made. In FIGS. 7b, 7c and 7d, these exit points are indicated by a looping arrow. This value is always adjusted by the Precision Multiplier (PrecMultRfunc) which is the input the user has to increase or decrease the average frequency of sampling.

StatusR=1 Oestrus Cycling with a Very Low Likelihood of Pregnancy (FIG. 7c)

This part of the reproductive model deals with three conditions: oestrus, prolonged follicular phase and prolonged luteal phase.

The Follicular Phase (Low Progesterone)

Once the cow is cycling, oestrus is defined by the first occurrence of a progesterone level below LThreshR. It is assumed that oestrus cannot occur if progesterone is above LThreshR irrespective of any other oestrus signs. Identification of oestrus causes a change in reproductive status to StatusR=2, potentially pregnant irrespective of any insemination.

In order to prevent oestrus being indicated for each successive progesterone below LThreshR a counter (CountR) is used and oestrus is only indicated for the first progesterone value below LThreshR. For oestrus to be indicated, there may be a requirement that the slope of the progesterone profile (SlopeR) is less than a threshold (SThreshR). Once oestrus has been indicated, the model estimates how long to wait before inseminating (TimeToAIR) and the likelihood of the proposed insemination being successful (LikeAlSuccR). The default time lag to II is the assumed oestrus to ovulation interval, OestOvuIntR, this is then reduced if there is any indication of behavioural oestrus (EODR). The likelihood of the proposed insemination being successful (LikeAlSuccR) is based on an ideal conception rate (MaxConR) which can then be reduced by 4 different factors: energy status, oestrus number, length of the previous oestrus cycle, and the slope of the progesterone profile.

CyclenR is a smoothed value for the cycle length which would be expected from previous cycle lengths for that cow. CyclenR is updated at each oestrus. Additionally, at oestrus; the oestrus number (OestNR) is increased by 1, CountR is increased by 1 (thus preventing a repeat oestrus indication within that follicular phase), the date of the previous oestrus (DayOestR) is stored in OldOestR and updated to the current oestrus date. Finally, StatusR may be set to 2 and days to next sample may be set to (2×OestOvuIntR+1). It is important to note that although Status has changed to 2 this part of the program (StatusR=2) is not entered into until the next run.

A following (consecutive) run may come down the "oestrus path" because of a following low progesterone sample (LevelR is <LThreshR) or because the following run was triggered by an EOD entry (and the cow was found to not be potentially pregnant). In both of these cases CountR is greater than 1 i.e. oestrus has already been indicated within this follicular period (assuming that SlopeR was greater than SThreshR). The length of the follicular phase is updated by adding the interval from the last to the current run to FolPerR. At the same time, the length of the following luteal period (LutPerR) may be updated to be zero and DayoestR is adjusted to Date—OestOvuIntR. In the luteal phase LutPerR will be incremented by IntR. Following oestrus, the next sample is taken 2×OestOvuIntR.

If the EOD is above EThreshR then it might be worth updating the TimetoAI calculation. In this case no need to revise the previous days to next sampling value is perceived. If the reason for being in this part of the model is because of a longer follicular period i.e. EOD<EThreshR, then the risk of a prolonged follicular phase (RiskFolR) and the days to next sampling (DNSR) are calculated on the basis of the length of the follicular period. The longer FolPerR, the shorter the interval to next sampling.

The Luteal Phase (High Progesterone)

This part of the model controls the sampling frequency in the luteal phase and calculates the risk of a prolonged luteal phase i.e., a luteal cyst. This part of the model first deals with a potential contra-indication, namely a high EOD during the luteal phase. If the latest progesterone value is high (above LThreshR) and the current run is triggered by a high EOD (above EThreshR) then something doesn't match. This is resolved by setting Days to Next sample to 0 to verify the progesterone level. Implicit in this is the assumption that a true high EOD cannot occur if progesterone is high.

The length of the luteal phase is accumulated by the time since the previous run if LevelR is above LThreshR. The Risk of a luteal cyst (RiskLutR) is calculated on the basis of the length of the current luteal phase relative to that expected from CyclenR. RLutLagR is a constant for the average length of the follicular phase. The finding that retained placenta predisposes for luteal cysts should be incorporated as a multiplier. In the luteal phase, Days to Next Sample (DNSR) is calculated from Cyclen and the slope of progesterone (SlopeR) such that increasing days since last oestrus and a more negative slope both decrease the DNSR. The days to next sample decreases the longer the interval since last oestrus. If the system detects a decline in progesterone i.e., SlopeR is negative, then DNSR is reduced. The more negative the slope the shorter the DNSR.

StatusR=2 Potentially Pregnant (FIG. 7d)

The change to StatusR=2 could be triggered in 2 ways; because an oestrus is detected or because an insemination has been recorded. Making Status 2 a consequence of a detected oestrus means that the cow is assumed to be potentially pregnant prior to any information about an insemination. The reason for this relates back to the underlying premise that progesterone is the definitive measure of reproductive status. In other words, this way of initiating Status 2 ensures that all pregnancies start from an oestrus. However, it gets a bit messy if the subsequent model run is triggered by information other than a progesterone value such as EOD information within the oestrus period.

Making Status 2 conditional on the input of an insemination record means that the cow is considered to be in Status 1 until the insemination record has been entered, this makes accurate and timely insemination data input rather important. It requires a rather unsatisfying procedure for checking the validity of the insemination with respect to progesterone levels (which may be outdated by the time the AI is input).

Once StatusR=2, the likelihood of the cow being pregnant (LikePregR) is calculated on the basis of a timely AI (AITimeR), the progesterone level measured after the AI (LevTimeR), and any pregnancy determinations (PDR).

AITimeR describes the effect of mistiming insemination relative to oestrus where inseminations which are too early or too late are less likely to result in pregnancy. LevTimeR uses the progesterone values and the days since AI to indicate the likelihood that there is a pregnancy. This is a bit more complicated. Consider a given time after insemination eg. 5 days, at this time a progesterone level of 6 ng/ml would be considered a good sign that pregnancy had not failed. However, at 21 days after insemination 6 ng/ml would be considered a strong sign that pregnancy was failing. Therefore, it is necessary to make the relationship between progesterone level and likelihood of pregnancy a function of days since insemination.

As mentioned above, making the change to Status=2 a function of oestrus detection means that a likelihood of pregnancy may be calculated before an insemination data has been entered. This will cause the model to revert back to Status 1. In the case where the run is caused by a new progesterone sample this outcome is fine because the next progesterone sample is set to be somewhere around 5 days after the start of oestrus by which time if there has been no insemination then the cow is not pregnant. However, if the run is caused by something other than progesterone e.g., an EOD value, then there are no grounds for judging the cow not pregnant. This is dealt with by the use of a variable called WaitR which is initially set to be the date at which the next progesterone sample is due after oestrus is declared. In Status=2, if the current RunTime is less than WaitR then the model doesn't run the Status 2 calculations. WaitR is modified by the input of an insemination such that the status 2 calculations won't be run until probably 5 days after the insemination.

Pregnancy determination (PDR) is also included in the calculation of likelihood of pregnancy. At first sight it seems that a positive PDR is the most valuable but for likelihood of pregnancy it is actually the negative PDRs which are interesting ie. the cow is not pregnant. The PDR input is 0.1 for not pregnant, 0.5 for uncertain, and 1 for definitely pregnant. The default PDR could be 1, the cow is assumed to be pregnant in the absence of any contrary information. Thus, inputting a PDR=0.1 will probably cause the likelihood of pregnancy to be so low as to cause the cow to revert to Status 1. In other words, the PDR input allows the farmer to change the cows status back to cycling if he has good evidence that the cow is not pregnant.

Once the likelihood of pregnancy (LikePregR) has been calculated this is used to decide whether the cow should stay in Status 2 or revert to Status 1. If LikePregR is lower than a given threshold (PThreshR) then the cow is assumed to not be pregnant and the model loops back through Status 1 within the present model run. This is done in real time because at the point where it is first possible to definitively classify the cow as not pregnant (approx. 21 days post-insemination) the cow may already be showing her next oestrus.

If the cow is considered to still be potentially pregnant (StatusR=2) then days to next sample (DNSR) is calculated.

List of Inputs and Outputs

Suggested Inputs

| Parameter | Comment |
|---|---|
| CowID | Unique ID, duplicates not allowed |
| RunTimeR | The current time at which the model is activated. Clock synchrony issue here |
| ProgTimeR | Date and time of the latest Progesterone sample |
| LevelR | Concentration of Progesterone - smoothed output of SSM |
| SlopeR | rate of change in Progesterone - smoothed output of SSM |
| IntR | Time interval between the latest and the previous Progesterone samples - not always necessary because of keeping LastRunR as a recurrent. |
| EODtimeR | Date and time of and External Oestrus Detection |
| EODinR | Likelihood of oestrus based on external oestrus detection - a value between 0 and 1 |
| EODtypeR | The type of EOD system being used. Controls the accuracy of EODR and EODtimeR |
| PrecMultR | Precision Multiplier for reproduction |
| DFC | Days from Calving - should be validated against prior pregnancy and AI records. |
| Breed | Code for different breeds including "other" |
| Parity | 1, 2, or 3+ |
| ProbTypeR | Code for type of reproductive problem |

-continued

| Parameter | Comment |
| --- | --- |
| ProbDateR | Date of first identification |
| ProbSevR | Code for severity of problem: mild = 0.3, average = 0.6, severe = 0.9 |
| ProbCertR | Code for certainty of diagnosis: possible = 0.3, probable = 0.6, definite = 0.9 |
| EnStat | Energy status, output of another model |
| AIdateR | Date of latest insemination |
| PDdateR | Date of latest pregnancy determination |
| PDR | Code for outcome of pregnancy determination: Not pregnant = 0.1, Uncertain = 0.5, Pregnant = 1.0 |

Suggested Outputs to the End-User:

| Parameter | End-User | Comment |
| --- | --- | --- |
| DNSR | Merkur | Days to next sampling |
| DayOest1R | Herd Man. | needed for herd stats |
| ProAnRiskR | Cow Man. | Risk of Prolonged Anoestrus (cow level) |
| Oestrus | Cow Man. | indicate cows in oestrus |
| Inseminate | Cow Man. | suggested optimum time for AI (given oestrus) |
| LikeAISuccR | Cow Man. | Estimated likelihood of success if AIing |
| RiskLutR | Cow Man. | Risk of a luteal cyst |
| RiskFolR | Cow Man. | Risk of a follicle cyst |
| LikePregR | Cow Man. | Likelihood of pregnancy (given AI) |
| NotPregFlagR | Cow. Man | Flag changing back to Status 1 if more than 30 days post AI |
| Max(OestN) needs specifying | Herd Man. Developer | |

Figure 8:
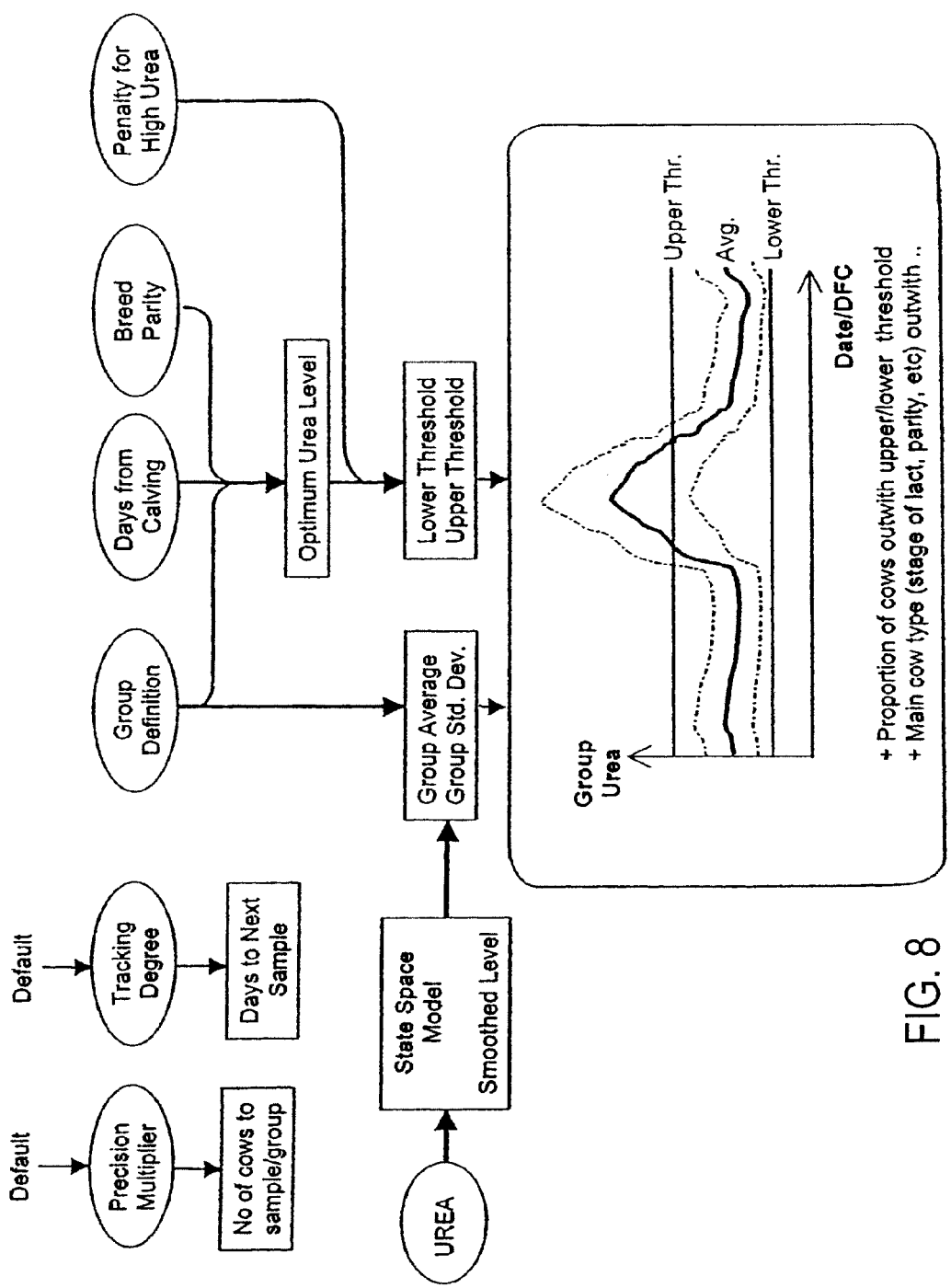
FIG. 8 shows information flow according to an embodiment of the present invention when analysing for urea and protein status.

Application of the Present Invention for the Determination of Urea and Protein Status:

In yet a preferred embodiment of the present invention urea and protein status is detected in animals, as shown in FIG. 8. The information provided by milk urea may be difficult to interpret without simultaneously considering energy status and having feed formulation information. The availability of this information will allow individual animal feeding.

Furthermore, as illustrated in FIG. 8, the biological model for urea is very simple. The reason for this is that there can be very little biological interpretation of urea data unless there is an associated evaluation of energy status. Furthermore, abnormal milk urea levels may be due to both problems in the balance of feed protein sources (protein quality) and imbalances in the ratio of protein to energy.

The purpose of the urea model presented here is to allow monitoring of milk urea levels on a group basis (monitoring on individual basis is also possible). This is expected to be useful relative to milk quality and environmental pollution regulatory requirements. The model consists of a biometric component to obtain smoothed individual cow urea values from which group averages are obtained.

Note: All the urea model parameter names end with a capital U (for Urea), drop the ending 'U' and they should be (to some degree) readable.

Group Definition

This should come from a Herd Management System i.e. farmer input. The farmer needs to input the relevant "physical group" for each cow. The "physical group" could be one or more of:

Physical location: the shed or subdivision of shed within which the cow is located.

Milking group: this would usually be the same as physical location.

Feeding group: this may not be the same as physical location if advanced feed distribution systems are present.

It is also envisaged that it should be possible to present results according to "biological group" i.e, groupings based on breed, parity and stage of lactation.

Urea Threshold Display

Given the biological group information and information from the literature a default optimum urea level for each biological group can be included in the model from which default upper and lower recommended urea levels will be generated for use as reference levels. These should be modifiable by the user to account for local conditions such as feed type and regulatory requirements.

Triggering a Run of the Model and Handling Sampling Frequency

Days to next sample is directly under the control of the user through the input of Tracking Degree. In addition, the user is also required to specify what proportion of each of the groups that requires or needs to be sampled. In this way it is possible to tailor the precision of the urea measurements to match the interest in milk urea levels.

Presentation of Group Urea Results

The end-user should be able see the progression of group urea levels relative to both calendar date and days from calving (DFC). Thus, calculation of average (AvgLevelU) and standard deviation (StdLevelU) of urea level should be done for each DFC or each calendar date. It could also be useful to characterise which type of cow ie., biological group, is dominant in the tails of the distribution of urea levels. It will also require that the cows chosen for urea sampling are evenly distributed across the relevant biological groups.

List of Inputs and Outputs

Suggested Inputs

| Parameter | Comment |
| --- | --- |
| CowID | Unique ID, duplicates not allowed |
| UreaTimeU | Date and time of the latest Urea sample |
| LevelU | Concentration of Urea - smoothed output of SSM |
| PrecMultU | no of sample/group |
| DNSU | tracking degree |
| Group | physical group definition |
| DFC | Days from Calving - should be validated against prior pregnancy and AI records. |
| Breed | Code for different breeds including "other" |
| Parity | 1, 2, or 3+ |
| UpThreshU | Recommended upper urea level |
| LoThreshU | Recommended lower urea level |

Suggested Outputs to the End-User:

| Parameter | Comment |
| --- | --- |
| GroupTime | the days from calving, or calendar date, to which the average urea etc relate |
| AvgLevelU | Group Average Urea |
| StdLevelU | Group standard deviation Urea |

Figure 9:
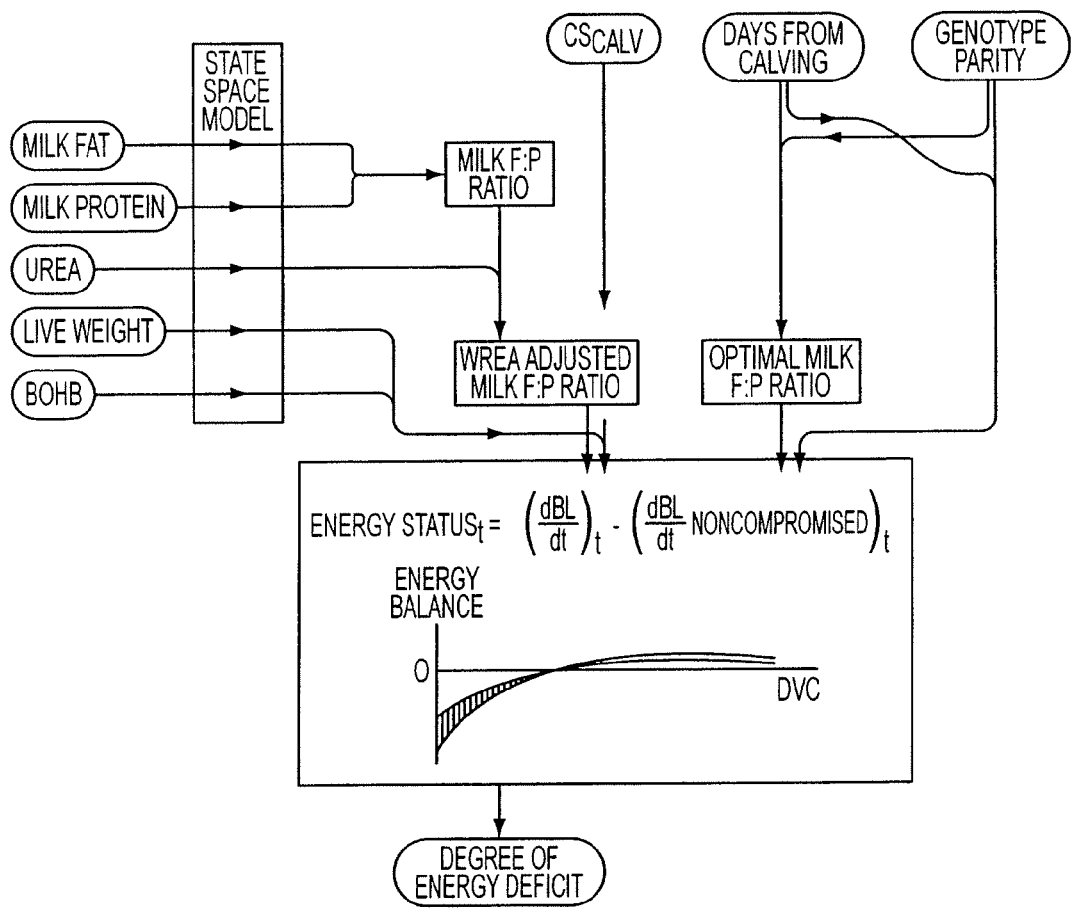
FIG. 9 shows information flow according to an embodiment of the present invention when analysing for milk fat, milk protein and energy status.

Application of the Present Invention for the Determination of Milk Fat, Milk Protein, and Energy Status:

In another preferred embodiment of the present invention milk fat, milk protein, and energy status is detected in animals, as shown in FIG. 9. Energy status is defined as the size of the body lipid (energy) mobilisation which is in excess of that mobilisation which is totally natural for a cow in a non compromising situation. This is depicted in the graph, the energy status equation, correspond to the hatched components of the graph. It is anticipated that the non-compromised rate of body mobilisation can be derived with reasonable accuracy from information about genotype, parity and days from calving. However, measuring total body loss (dBL/dt) in real time is a rather more daunting prospect. Milk fat:protein ratio should provide an indicator especially when used in conjunction with urea measurements.

An alternative model could be established for milk fat and protein.

The cost per sample of measuring a parameter is normally relatively high and the models described therefore needs to be able to run in a stable way when the frequency of sampling is very low. At low frequencies the performance of the state space model may be substantially reduced. Therefore, the number of parameters and external parameters included in the model may be variable which will e.g. be dependent on the national requirements regarding accuracy and precision of the measurement.

The described non-limiting models of how to detect a selected parameter should not be limited to the described models as it is obvious to the person skilled in the art how to modify and optimise the models. Furthermore, the scope of the present invention is not limited to the parameters (BHB, Mastitis Indicator (e.g, LDH or NAGase), progesterone, urea, protein status, milk fat, milk protein and energy status) which has been additionally explained above.

EXAMPLES

In order to illustrate the methodology, data $\{y_t\}_{t=1,\ldots,50}$ were generated according to the linear growth model with exceptions, conditional on $M_t(j)$, given by observation equation: $Y_t = F_t \theta_t + v_t$, with $F_t = (1\ 0)$ and $\theta_t = (\mu_t, \beta_t)'$; system equation (s) $\mu_t = \mu_{t-1} + \beta_t + \epsilon_{\mu,t}$ and $\beta_t = \beta_{t-1} + \epsilon_{\beta,t}$ with $v_t | M_t(j) \sim N(0, V(j))$, $\epsilon_{\mu,t} | M_t(j) \sim N(0, E_\mu(j))$ and $\epsilon_{\beta,t} | M_t(j) \sim N(0, E_\epsilon(j))$, $j=1,\ldots,4$ and $t=1,\ldots,50$ assumed to be mutually independent.

In FIG. 3, chart A depicts simulated data, chart B depicts posterior probabilities of the 4 different models at time $t= 1,\ldots,50$, and charts C and D depict one and two step back smoothed probabilities of the 4 different models at time $t= 1,\ldots,49$ and time $t=1,\ldots,48$, respectively.

$$\left( \theta_t = \begin{pmatrix} 1 & 1 \\ 0 & 1 \end{pmatrix} \theta_{t-1} + w_t \text{ with } w_t \middle| M_t(j) \sim N_2(0, W_t(j)); \right.$$

$$W_t(j) = \begin{pmatrix} E_\mu(j) + E_\beta(j) & E_\mu(j) \\ E_\mu(j) & E_\mu(j) \end{pmatrix} \right)$$

Values of the different parameters are given in Table 1. $\theta_0$ was arbitrary set to $(4\ 0)'$ and all of the data were simulated from Model 1 (steady state) except for a change in level at time 10, a change in slope at time 25 and an outlier at time 40. The parameters from Table 1 were used in the analysis and the initial information was (arbitrary) assumed to be $$\theta_0 \sim N_2\left( \begin{pmatrix} 4 \\ 0 \end{pmatrix}, \begin{pmatrix} 20 & 0 \\ 0 & 10 \end{pmatrix} \right).$$

TABLE 1

Parameters used for analysing simulated data.

| Model j | Name | $\pi_0(j)$ | V(j) | $E_\mu(j)$ | $E_\beta(j)$ |
|---|---|---|---|---|---|
| 1 | steady state | 0.94 | 1.0 | 0.0 | 0.0 |
| 2 | chance in level | 0.02 | 1.0 | 20.0 | 0.0 |
| 3 | change in slope | 0.02 | 1.0 | 0.0 | 10.0 |
| 4 | outlier | 0.02 | 50.0 | 0.0 | 0.0 |

The simulated data are shown in FIG. 3.A. Posterior probabilities (FIG. 3.B) of the outlier model are very high at times 10, 25 and 40. I.e. abrupt changes are detected—but not the true nature of the changes. The outlier is pointed out (without false positive detections of outliers) from one step back smoothed probabilities (FIG. 3.C). Finally from two step back smoothed probabilites (FIG. 3.D) high probabilities of the models used in the simulation are obtained at all time-points.

There is thus provided modelling and monitoring of biological time series subject to outliers and changes in the underlying latent variables presented in Smith and West (1983). Smith and West used the method successfully to provide on-line probabilities of serious changes in kidney function in individual patients who had recently received transplants. However, it has been found that the method is relevant in agriculture. For example, based on regular measurement of ln(somatic cell count), or other indicators of mastitis, it is possible to provide probabilities of mastitis and to detect mastitis earlier and more reliably than with other methods due to the flexibility of the models. In applications of multiprocess II mixture models, parameters have been found from empirical trials with the system (see e.g. Smith and West (1983) and Thysen (1992)). Moreover, information from relatives may be incorporated in mixture models, and breeding value estimation may be integrated.

Though, in the above discussion, cows have been mentioned as an example of animals, it should be understood that the discussed principles and features apply equally well to other especially domestic animals, including sheep, goat, buffalo, camel, pig, horse, and chicken.

REFERENCES

Harrison P. J., Stevens C. F. (1976) J. of the Stat. Soc. Ser. B 38, 205-247.
Smith A. F. M., West M. (1983) Biometrics 39, 867-878.
Thysen I. (1993) Acta Agric. Scand. Sect. A., Animal Sci. 43, 58-64.
U.S. Pat. No. 6,405,672
R. M. de Mol (2000), "Automated detection of oestrus and mastitis in dairy cows".

The invention claimed is:
1. A system for selecting a point in time for providing a sample from an animal, the system comprising:
   a computer comprising a processor and being operatively connected to a database,
   at least one sample providing device for repetitively providing at least one sample of a body fluid of the animal,
   an analysis apparatus for analyzing the at least one sample, so as to obtain at least one sample value of at least one parameter of the body fluid,
   a data interface for repetitively entering the sample value of the at least one parameter in the database, wherein the database is adapted to store multiple database entries representing the sample value of the at least one parameter at various points in time, and wherein the processor is programmed to:
  perform at least one mathematical analysis of the at least one sample value, and
  compare the at least one mathematical analysis with a pattern in measured parameters in order to select the point in time for providing a subsequent sample and performing a subsequent analysis of said subsequent sample for at least one of the parameters.

2. A system according to claim 1, wherein the mathematical analysis is a statistical analysis.

3. A system according to claim 2, wherein the statistical analysis comprises a univariate analysis of the database entries to obtain a first set of data representing expected sample values of at least one of the parameters at future points in time.

4. A system according to claim 3, wherein the statistical analysis comprises a multivariate analysis of the database entries to produce a second set of data derived from combined analysis of sample values of at least two parameters.

5. A system according to claim 4, wherein the first and second sets of data are combined to obtain a third set of data representative of the physiological state of the animal.

6. A system according to claim 5, wherein the obtained first, second and third sets of data are stored in the database.

7. A system according to claim 3, wherein the processor is programmed to perform the univariate analysis employing at least one State Space Model (SSM).

8. A system according to claim 4, wherein the multivariate analysis is Principal Component Analysis (PCA).

9. A system according to claim 5, wherein the database stores at least one predetermined set of data representing at least one physiological state of the animal, and wherein the processor is further programmed to compare the third set of data to the at least one predetermined set of data.

10. A system according to claim 1, wherein the at least one sample of the body fluid comprises at least one raw milk sample, and wherein the at least one sample providing device is arranged to provide the raw milk sample.

11. A system according to claim 1, wherein the analysis apparatus is arranged to perform spectroscopic analysis of the sample of the body fluid of the animal.

12. A system according to claim 11, wherein the analysis apparatus performs analysis in a near- or mid-infrared spectrum.

13. A system according to claim 1, wherein the analysis apparatus comprises solid support analytical devices.

14. A system according to claim 1, wherein the analysis apparatus is arranged to determine the sample value(s) of at least one parameter selected from the group consisting of: LDH, NAGase, Progesterone, milk yield, FPD and Conductivity, Fat A, Fat B, Protein, Lactose, Urea, Citric Acid, TS, SNE, and one or more of the ketone bodies in the one or more samples.

15. A system according to claim 1, wherein the database comprises at least one external value of at least one external parameter.

16. A system according to claim 15, wherein the at least one external parameter is selected from the group of parameters consisting of the age of the animal, the breed or race of the animal, the weight of the animal, the reproduction of the animal, feeding particulars, season and geographical location, and identification to the herd of origin.

17. A system according to claim 15, wherein the processor is further programmed to perform data analysis of the database entries to obtain an indication of the physiological state of the animal, whereby the external value is included in the data analysis.

18. A method for selecting a point in time for providing a sample from an animal, the method comprising:
  repetitively obtaining, from a providing device, at least one sample of a body fluid of the animal,
  supplying the at least one sample to an analyzing apparatus and analyzing the at least one sample, so as to obtain at least one sample value of at least one parameter of the body fluid,
  entering the sample value of the at least one parameter in a database of a computer system, wherein the computer system comprises a processor and is operatively connected to the database, and wherein the database is loaded with multiple database entries representing the sample value of the at least one parameter at various points in time,
  performing at least one mathematical analysis of the at least one sample value, and
  selecting, on the basis of the at least one mathematical analysis, the point in time for providing a subsequent sample and performing a subsequent analysis of said subsequent sample for at least one of the parameters.

19. A method according to claim 18, wherein the mathematical analysis is a statistical analysis.

20. A method according to claim 19, wherein the statistical analysis comprises a univariate analysis of the database entries to obtain a first set of data representing expected sample values of at least one of the parameters at future points in time.

21. A method according to claim 20, wherein the statistical analysis comprises a multivariate analysis of the database entries to produce a second set of data derived from combined analysis of sample values of at least two parameters.

22. A method according to claim 21, wherein the first and second sets of data are combined to obtain a third set of data representative of the physiological state of the animal.

23. A method according to claim 22, wherein the obtained first, second and third sets of data are stored in the database.

24. A method according to claim 20, wherein the univariate analysis is performed in at least one State Space Model (SSM).

25. A method according to claim 24, wherein the State Space Model provides probabilities of changes.

26. A method according to claim 21, wherein the multivariate analysis is Principal Component Analysis (PCA).

27. A method according to claim 21, wherein, in the multivariate analysis, at least two disjoint sets of Principal Components are selected.

28. A method according to claim 21, wherein the computer system is programmed to perform the multivariate data analysis using a Partial Least Squares Regression model (PLSR model).

29. A method according to claim 21, wherein a mathematical model of the form $$X = T_a * P_a' + E$$

is used in the multivariate data analysis, wherein X represents the scaled or otherwise pre-processed matrix of the sample values, T represents latent variables, P is the eigenvector of a correlation matrix determined as X'X, and E is a residual matrix which collects random noise, and a denotes a dimension of the model.

30. A method according to claim 29, wherein sample values are sampled in a pattern $X_i$, and wherein the projection of $X_i$ on each of the models, $t_i$, is determined as $t_i = X_i * P$.

31. A method according to claim 30, wherein:
a leverage h, is determined as the square sum of the elements of $t_i$, a residual r is determined as the square sum of the elements a vector determined as $x_i-t_i*P$,
the quantities h and r are normalized with their respective 95% significance levels for the mathematical model, and wherein
$X_i$ is chosen to belong to the model in question if the length of vector (h,r) is less than $-\sqrt{2}$.

32. A method according to claim 18, wherein a dynamic linear model is extended to a multiprocess class II mixture model with a recursive updating procedure.

33. A method according to claim 18, wherein the at least one sample of a body fluid comprises at least one raw milk sample, and wherein the at least one sample providing device provides the raw milk sample.

34. A method according to claim 18, comprising, at the step of analyzing the at least one sample, performing spectroscopic analysis of the sample of body fluid.

35. A method according to claim 34, wherein the spectroscopic analysis comprises near- or mid-range infrared analysis.

36. A method according to claim 18, wherein historical sample values are grouped in classes, and wherein the classes are analyzed individually by means of Principal Component Analysis.

37. A method according to claim 18, wherein the physiological state is determined from a comparison of a pattern in the sample values and a pattern of reference parameter values which is typical for a certain predetermined physiological state.

38. A method according to claim 18, wherein the sample value(s) of at least one or more parameter is selected from the group consisting of: Nagase, Progesterone, milk yield, FPD and Conductivity, Fat A, Fat B, Protein, Lactose, Urea, Citric Acid, TS, SNE, and one or more of the ketone bodies is/are determined in the analysis apparatus.

39. A method according to claim 18, wherein the database entries further comprise at least one external value of at least one external parameter, and wherein the multivariate data analysis employs the at least one external value.

40. A method according to claim 39, wherein the at least one external parameter comprises at least one of: the age of the animal, the breed or race of the animal, the weight of the animal, the reproduction of the animal, feeding particulars, season, and geographical location, and identification to the herd of origin.

41. A method according to claim 39, wherein the method further comprises the step of performing data analysis of the database entries to obtain an indication of the physiological state of the animal, whereby the external value is included in the data analysis.

42. A method according to claim 18, wherein the database stores at least one predetermined set of data representing at least one physiological state of the animal, and wherein the processor is further programmed to compare the third set of data to the at least one predetermined set of data.

43. A method according to claim 18, wherein physiological state of the animal is observed or predicted from comparing the at least one mathematical analysis with a reference pattern which is typical for healthy animals and a pattern which is typical for animals suffering from a certain disease.

44. A method for selecting a point in time for providing a sample from an animal, the method comprising:
repetitively obtaining, from a providing device, at least one sample of a body fluid of the animal,
supplying the at least one sample to an analyzing apparatus and analyzing the at least one sample, so as to obtain at least one sample value of each of a plurality of parameters of the body fluid,
entering the sample value of each of the parameters in a database of a computer system, wherein the computer system comprises a processor and is operatively connected to the database, and wherein the database is loaded with multiple database entries representing the sample value of each of the parameters at various points in time,
performing State Space Model (SSM) analysis of the database entries to obtain data representative of the physiological state of the animal, and
comparing the data from the State Space Model (SSM) analysis with a pattern in measured parameters in order to select the point in time for providing a at least one subsequent sample of a body fluid of the animal and performing a subsequent analysis of said at least one subsequent sample to obtain at least one sample value of each of a plurality of parameters.

45. A method according to claim 44, wherein physiological state of the animal is observed or predicted from comparing the data from the State Space Model (SSM) analysis with a reference pattern which is typical for healthy animals and a pattern which is typical for animals suffering from a certain disease.

46. A method for selecting a point in time for providing a sample from an animal, the method comprising:
repetitively obtaining, from a providing device, at least one sample of a body fluid of the animal,
supplying the at least one sample to an analyzing apparatus and analyzing the at least one sample, so as to obtain at least one sample value of each of a plurality of parameters of the body fluid,
entering the sample value of each of the parameters in a database of a computer system, wherein the computer system comprises a processor and is operatively connected to a database, and wherein the database is loaded with multiple database entries representing the sample value of each of the parameters at various points in time,
performing at least one of a Principal Component Analysis and a Partial Least Squares Regression of the database entries to obtain data representative of the physiological state of the animal, and
comparing the data from the at least one of a Principal Component Analysis and a Partial Least Squares Regression analysis with a pattern in measured parameters in order to select the point in time for providing at least one subsequent sample of a body fluid of the animal and performing a subsequent analysis of said at least one subsequent sample to obtain at least one sample value of each of a plurality of parameters.

47. A method according to claim 46, wherein physiological state of the animal is observed or predicted from comparing the data from the at least one of a Principal Component Analysis and a Partial Least Squares Regression analysis with a reference pattern which is typical for healthy animals and a pattern which is typical for animals suffering from a certain disease.

* * * * *